US012799268B2

(12) United States Patent
Ramprasad et al.

(10) Patent No.: US 12,799,268 B2
(45) Date of Patent: Nov. 17, 2026

(54) POLYMER DESIGNS FOR HIGH ENERGY DENSITY APPLICATIONS WITH HIGH DIELECTRIC STRENGTH AND DIELECTRIC CONSTANT AT HIGH TEMPERATURE

(71) Applicant: Georgia Tech Research Corporation, Atlanta, GA (US)

(72) Inventors: Rampi Ramprasad, Atlanta, GA (US); Rishi Gurnani, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 496 days.

(21) Appl. No.: 18/513,017

(22) Filed: Nov. 17, 2023

(65) Prior Publication Data

US 2024/0174791 A1 May 30, 2024

Related U.S. Application Data

(60) Provisional application No. 63/384,261, filed on Nov. 18, 2022.

(51) Int. Cl.
*C08G 61/08* (2006.01)
*C08G 61/12* (2006.01)
(Continued)

(52) U.S. Cl.
CPC ........... *C08G 61/08* (2013.01); *C08G 61/125* (2013.01); *G06F 30/27* (2020.01); *G16C 20/30* (2019.02); *G16C 60/00* (2019.02); *C08G 2261/11* (2013.01); *C08G 2261/148* (2013.01); *C08G 2261/1646* (2013.01); *C08G 2261/3342* (2013.01); *C08G 2261/418* (2013.01); *C08G 2261/65* (2013.01)

(58) Field of Classification Search
CPC ........ C08G 61/08; C08G 61/12; G16C 20/30; G16C 20/70; G16C 60/00
See application file for complete search history.

(56) References Cited

U.S. PATENT DOCUMENTS

2016/0276060 A1* 9/2016 Flores .................. C08F 232/00
2020/0395102 A1* 12/2020 Minami ................ C08F 110/02
(Continued)

OTHER PUBLICATIONS

Park et al., "Syntheses and characterization of functionalized polynorbornene dicarboximides for flexible substrates," Polymers for Adv. Techs. 24, 249-257 (Year: 2012).*
(Continued)

*Primary Examiner* — Kregg T Brooks
(74) *Attorney, Agent, or Firm* — TROUTMAN PEPPER LOCKE LLP; Ryan A. Schneider; Elsie Yang

(57) ABSTRACT

An exemplary embodiment of the present disclosure provides a method of designing a polymer. The method can include: providing a set of polymer data; generating a set of polymer structures; providing one or more target properties for the polymer, predicting properties of each polymer structure of the set of polymer structures, and design considerations for the set of polymer structures; and selecting one or more polymer structures from the set of polymer structures, based at least in part, on the predicted properties of the polymer structures. The polymer data can include a set of monomer structures.

13 Claims, 31 Drawing Sheets

(51) Int. Cl.
*G06F 30/27* (2020.01)
*G16C 20/30* (2019.01)
*G16C 60/00* (2019.01)

(56) References Cited

U.S. PATENT DOCUMENTS

| | | | | |
|---|---|---|---|---|
| 2024/0290439 | A1* | 8/2024 | Aonuma | G16C 20/30 |
| 2026/0088140 | A1* | 3/2026 | Moon | G06N 3/08 |

OTHER PUBLICATIONS

Wolf et al., "Examiining the Effects of Monomer and Catalyst Structure on the Mechanism of Rutheniium-Catalyzed Ring-Opening Metathesis Polymerization," J. Am. Chem. Soc. 141, 17796-17808 (Year: 2019).*

* cited by examiner

700

POLYMER DESIGNS FOR HIGH ENERGY DENSITY APPLICATIONS WITH HIGH DIELECTRIC STRENGTH AND DIELECTRIC CONSTANT AT HIGH TEMPERATURE

CROSS-REFERENCE TO RELATED APPLICATIONS

This application claims the benefit of U.S. Provisional Application Ser. No. 63/384,261, filed on 18 Nov. 2022, which is incorporated herein by reference in its entirety as if fully set forth below.

GOVERNMENT LICENSE RIGHTS

This invention was made with government support under Agreement No. AWD-101931, awarded by the Office of Naval Research, a Multi-University Research Initiative (MURI) grant (N00014-171-2656), the Center for Understanding and Control of Acid Gas Induced Evolution of Materials for Energy (UNCAGE ME, an Energy Frontier Research Center) funded by the U.S. Department of Energy (DOE) under Award # DE-SC0012577, and by the National Science Foundation under grant 1941029. The government has certain rights in the invention.

FIELD OF THE DISCLOSURE

The various embodiments of the present disclosure relate generally to polymers and more particularly to polymer designs for high energy density applications.

BACKGROUND

High energy density capacitors that make use of polymer dielectrics are found in many different applications, including, but not limited to, hybrid and electric vehicles (as a buffer to batteries), pulsed electrical system used for food preservation, medical defibrillators, power grid electrification systems, and in pulsed power defense systems. In many of these applications, it can be desirable for the polymer dielectrics to be capable of withstanding high electric fields at high temperatures, while possessing a high dielectric constant.

The maximum electric field that can be applied to a dielectric polymer without destroying its insulating characteristics is known as the dielectric breakdown strength. This property, along with its dielectric constant sets an upper limit on the maximum electrostatic energy that can be stored in a capacitor. Such high energy density polymer dielectrics are favored in high power, high energy density, capacitors. Recently, there is also a need for such polymers to function well at high temperatures. A world with increasingly demanding high power electronics at high temperatures necessitates the development of polymers with breakdown strengths, dielectric constant, and thermal stability that surpass the limits of commercially available materials.

For example, the current standard dielectric material is biaxially oriented polypropylene (BOPP), which has a high breakdown strength (700 V/μm) and low dielectric loss (0.0001), but has a low dielectric constant (2.2), energy density (5 J/cc), and low temperature performance. Accordingly, there is a need to provide improved materials with high dielectric constant, high breakdown strength (high band gap) and high temperature operation.

Various embodiments disclosed herein provide such materials.

BRIEF SUMMARY

An exemplary embodiment of the present disclosure provides a dielectric polymer. The dielectric polymer can have a structure disclosed in any of the appended drawings.

In any of the embodiments disclosed herein, X can be oxygen, wherein $R_1$ can be a methyl group, wherein $R_2$ can be chlorine, wherein $R_3$ can be hydrogen, wherein R4 can be hydrogen, and wherein R5 can be hydrogen.

In any of the embodiments disclosed herein, X can be carbon, wherein $R_1$ can be a methyl group, wherein $R_2$ can be chlorine, wherein $R_3$ can be hydrogen, wherein R4 can be hydrogen, and wherein R5 can be hydrogen.

In any of the embodiments disclosed herein, wherein X can be carbon, wherein $R_1$ can be hydrogen, wherein $R_2$ can be chlorine, wherein $R_3$ can be a methyl group, wherein $R_4$ can be hydrogen, and wherein $R_5$ can be hydrogen.

In any of the embodiments disclosed herein, X can be a carbon, wherein $R_1$ can be a methyl group, wherein $R_2$ can be a methyl group, wherein $R_3$ can be hydrogen, wherein R4 can be hydrogen, and wherein R5 can be hydrogen.

In any of the embodiments disclosed herein, X can be a carbon, wherein R1 can be hydrogen, wherein R2 can be chlorine, wherein R3 can be hydrogen, wherein R4 can be hydrogen, and wherein R5 can be chlorine.

In any of the embodiments disclosed herein, the dielectric polymer can have a band gap of at between 4.0 eV and 5.0 eV.

In any of the embodiments disclosed herein, the dielectric polymer can have a $T_g$ of between 200 and 250 °C.

In any of the embodiments disclosed herein, the dielectric polymer can have a dielectric constant of 2.5-3.5.

In any of the embodiments disclosed herein, the dielectric polymer can achieve an energy density of 9 J/cc at 200 °C.

In any of the embodiments disclosed herein, the dielectric polymer can achieve an energy density greater than approximately 9 J/cc when the polymer is at a temperature between 0 °C and 100 °C, an energy density greater than approximately 8 J/cc when the polymer is at a temperature between 100 °C and 200 °C.

Another embodiment of the present disclosure provides a method of designing a polymer. The method can include: providing a set of polymer data; generating a set of polymer structures; providing one or more target properties for the polymer; predicting properties of each polymer structure of the set of polymer structures, and design considerations for the set of polymer structures; and selecting one or more polymer structures from the set of polymer structures, based at least in part, on the predicted properties of the polymer structures. The polymer data can include a set of monomer structures.

In any of the embodiments disclosed herein, the method further can further include synthesizing one or more polymers based on the selected one or more polymer structures.

In any of the embodiments disclosed herein, generating the set of polymer structures can include curating a database of available monomers and choosing a set of polymerization reactions.

In any of the embodiments disclosed herein, generating the set of polymer structures can further include simulating a transformation of the available monomers based on the polymerization reactions.

In any of the embodiments disclosed herein, providing the set of polymer data can include inputting the polymer data and the one or more target properties into a machine learning model. The method can further include updating the polymer data with the set of polymers and predicted properties of the set of polymer structures.

In any of the embodiments disclosed herein, the one or more target properties can include one or more of melting temperature, decomposition temperature, thermal conductivity, band gap, electron affinity, ionization energy, and solubility.

In any of the embodiments disclosed herein, the polymer data can include computational data and experimental data for a plurality of known polymers.

In any of the embodiments disclosed herein, generating the set of polymer structures can include applying one or more reaction templates to the set of monomer structures. The one or more reaction templates can include one or more of: an amide condensation, an ester condensation, an ether condensation, an imide condensation, a double nucleophilic aromatic substitution, a ring opening metathesis, and a click-chemistry based reaction template.

Another embodiment of the present disclosure provides a method of generating a structure for a polymer. The method can include curating a database of commercially-available monomer structures; selecting a polymerization reaction; selecting a subset of the database of monomer structures; simulating a transformation via the polymerization reaction of the monomer structures of the subset into a set of polymer repeat unit structures; predicting one or more respective properties of each polymer repeat unit structure of the set of polymer repeat unit structures; and selecting a polymer repeat unit structure of the set of polymer repeat unit structure based on the one or more respective properties.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

DESCRIPTION OF THE INVENTION

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

Figure 1A:
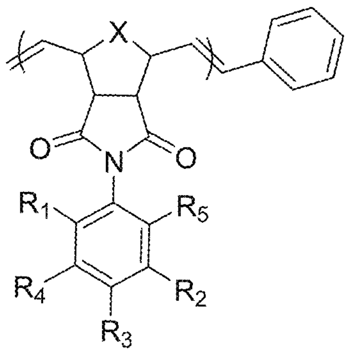
FIGS. 1A-1F provide chemical structures for dielectric polymers, in accordance with an exemplary embodiment of the present invention.

An exemplary embodiment of the present disclosure provides a dielectric polymer having the following structure depicted in FIG. 1A, wherein X is selected from oxygen and carbon, $R_1$ is selected from a methyl group, hydrogen, and chlorine, $R_2$ is selected from chlorine, a methyl group, and hydrogen, $R_3$ is selected from hydrogen and a methyl group, $R_4$ is selected from hydrogen and chlorine, and $R_5$ is selected from hydrogen and chlorine.

Figure 1B:
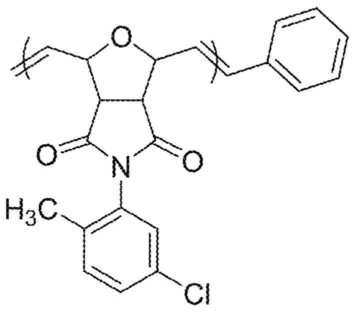

FIG. 1B depicts an embodiment of a dielectric polymer in which X is oxygen, wherein $R_1$ is a methyl group, wherein $R_2$ is chlorine, wherein $R_3$ is hydrogen, wherein R4 is hydrogen, and wherein R5 is hydrogen.

Figure 1C:
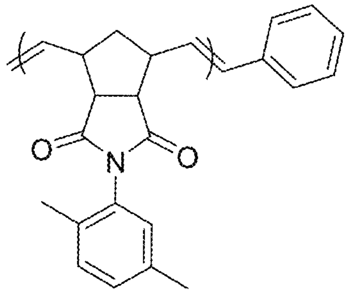

FIG. 1C depicts an embodiment of a dielectric polymer in which X is a carbon, wherein $R_1$ is a methyl group, wherein $R_2$ is a methyl group, wherein $R_3$ is hydrogen, wherein R4 is hydrogen, and wherein R5 is hydrogen.

Figure 1D:
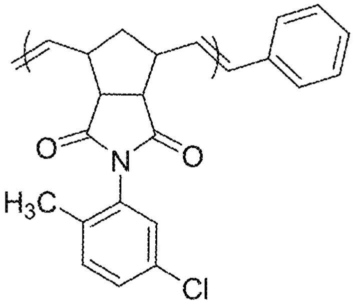

FIG. 1D depicts an embodiment of a dielectric polymer in which X is carbon, wherein $R_1$ is a methyl group, wherein $R_2$ is chlorine, wherein $R_3$ is hydrogen, wherein R4 is hydrogen, and wherein R5 is hydrogen.

Figure 1E:
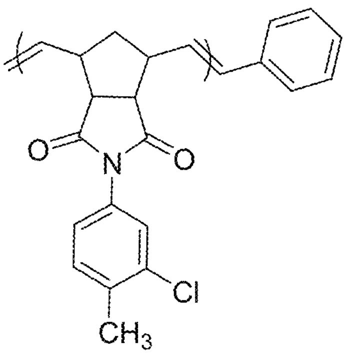

FIG. 1E depicts an embodiment of a dielectric polymer in which X is carbon, wherein $R_1$ is hydrogen, wherein $R_2$ is chlorine, wherein $R_3$ is a methyl group, wherein $R_4$ is hydrogen, and wherein $R_5$ is hydrogen.

Figure 1F:
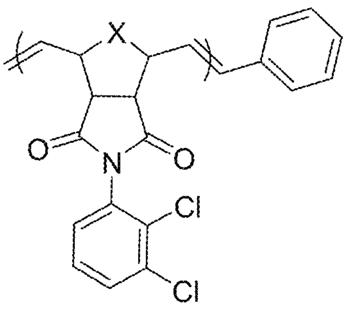
Figure 2A:
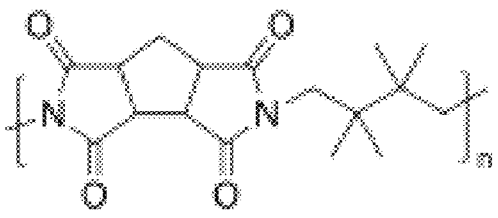
FIGS. 2A-2D provide chemical structures for dielectric polymers, in accordance with an exemplary embodiment of the present invention.
Figure 2B:
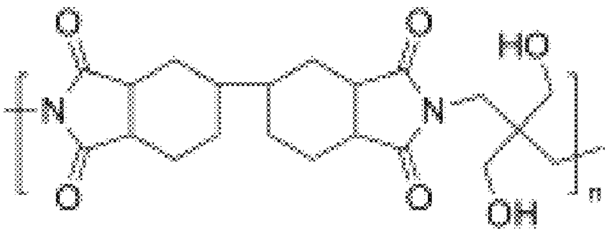
Figure 2C:
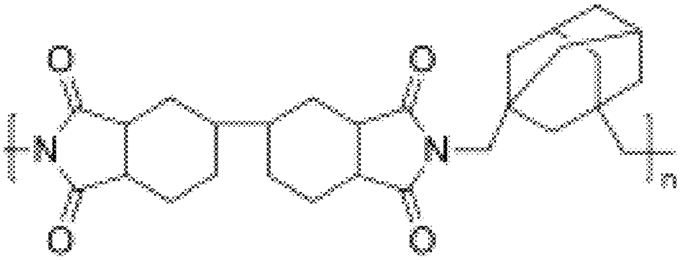
Figure 2D:
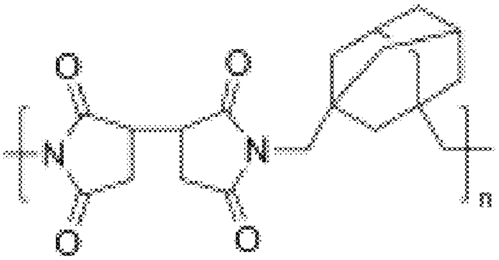

FIG. 1F depicts an embodiment of a dielectric polymer in which X is a carbon, wherein R1 is hydrogen, wherein R2 is chlorine, wherein R3 is hydrogen, wherein R4 is hydrogen, and wherein R5 is chlorine.

In any of the embodiments disclosed herein, the dielectric polymer can have a band gap of at between 4.0 eV and 5.0 eV.

In any of the embodiments disclosed herein, the dielectric polymer can have a $T_g$ of between 200 and 250 °C.

In any of the embodiments disclosed herein, the dielectric polymer can have a dielectric constant of 2.5-3.5.

In any of the embodiments disclosed herein, the dielectric polymer can achieve an energy density of 9 J/cc at 200 °C.

In any of the embodiments disclosed herein, the dielectric polymer can achieve an energy density greater than approximately 9 J/cc when the polymer is at a temperature between 0 °C and 100 °C, an energy density greater than approximately 8 J/cc when the polymer is at a temperature between 100 °C and 200 °C.

Figure 3A:
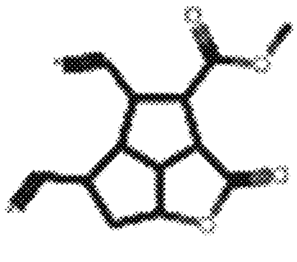
FIGS. 3A-T provide chemical structures for dielectric polymers, in accordance with an exemplary embodiment of the present invention.
Figure 3B:
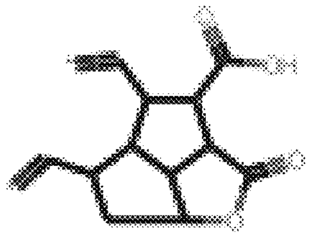
Figure 3C:
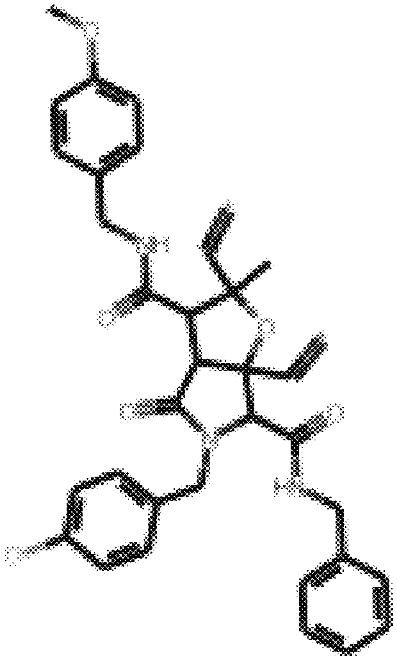
Figure 3D:
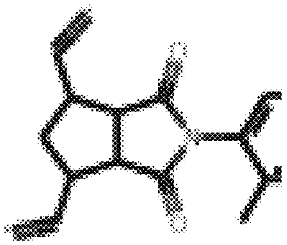
Figure 3E:
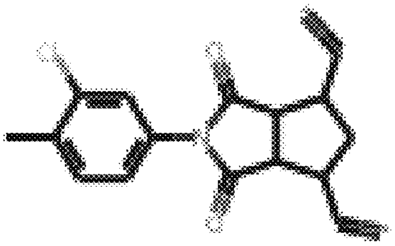
Figure 3F:
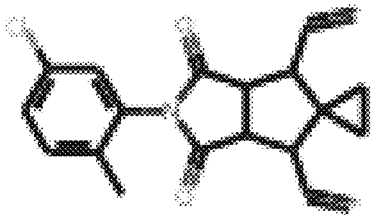
Figure 3G:
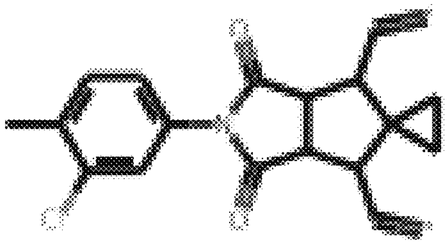
Figure 3H:
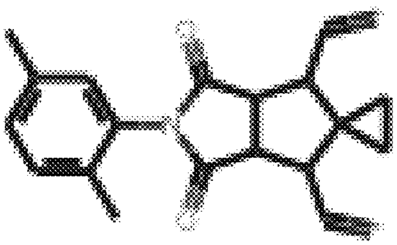
Figure 3I:
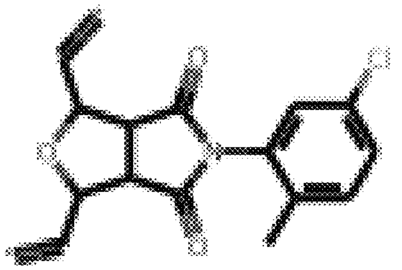
Figure 3J:
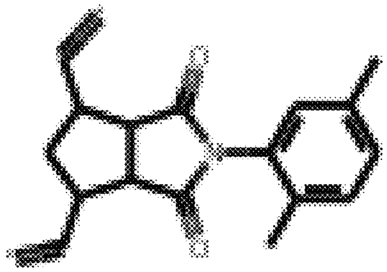
Figure 3K:
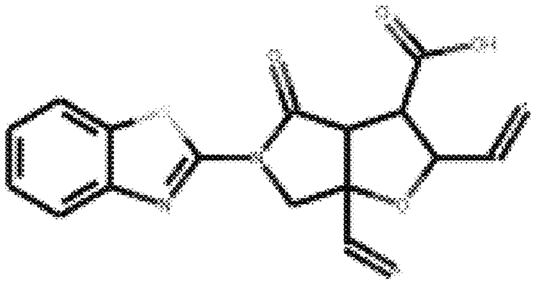
Figure 3L:
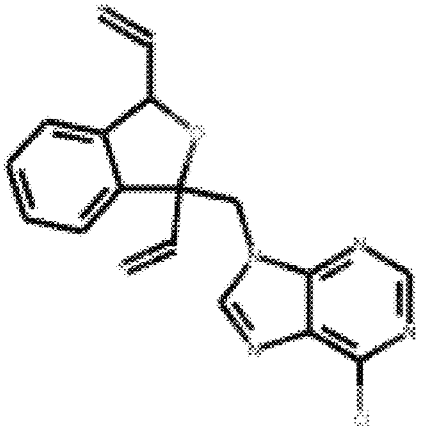
Figure 3M:
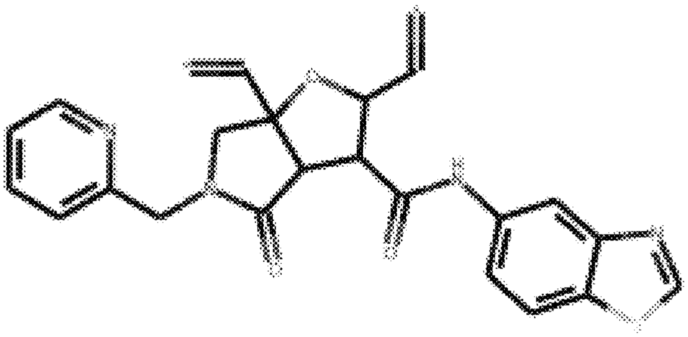
Figure 3N:
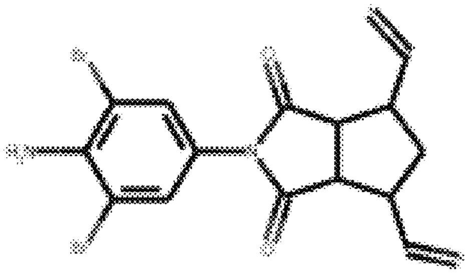
Figure 3O:
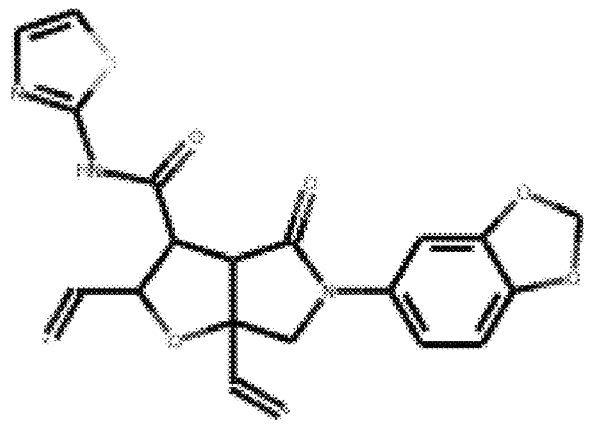
Figure 3P:
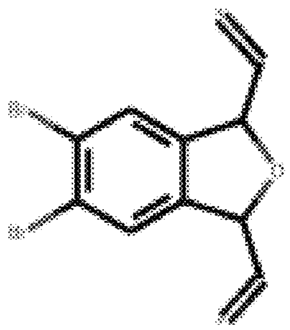
Figure 3Q:
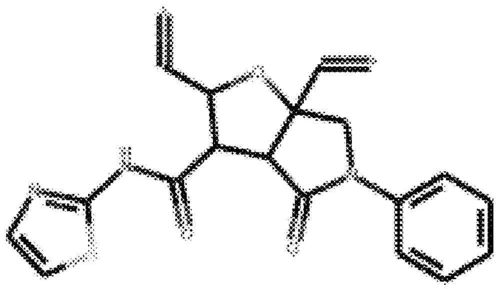
Figure 3R:
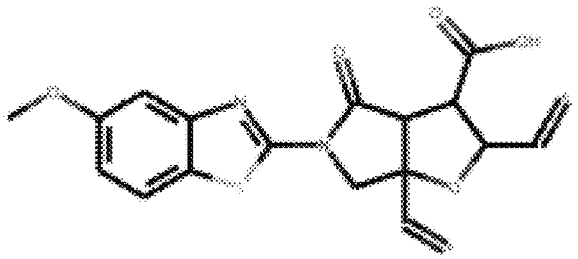
Figure 3S:
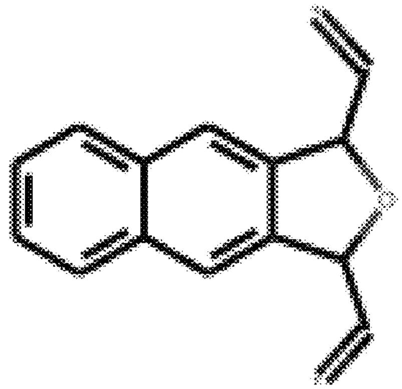
Figure 3T:
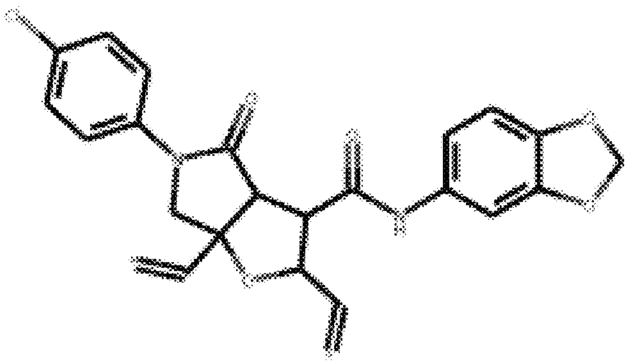
Figure 4A:
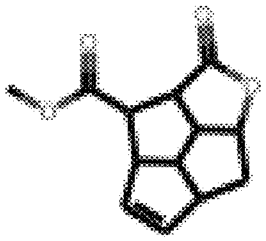
FIGS. 4A-4T provide chemical structures for respective monomers used to the polymers in FIGS. 3A-3T.
Figure 4B:
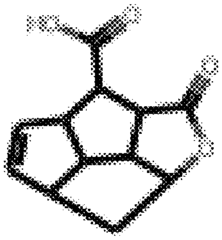
Figure 4C:
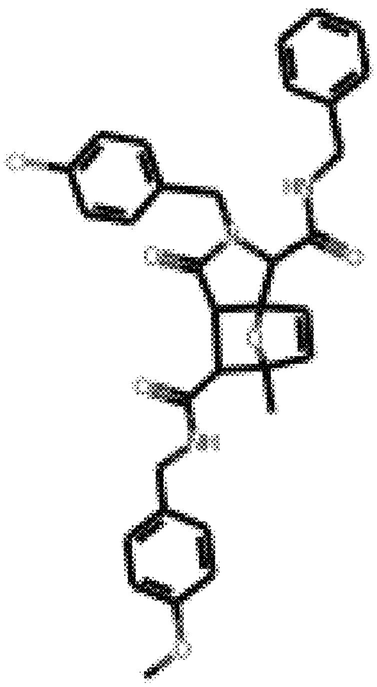
Figure 4D:
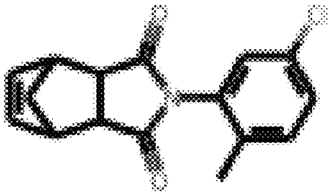
Figure 4E:
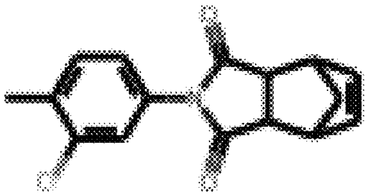
Figure 4F:
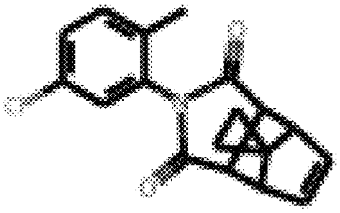
Figure 4G:
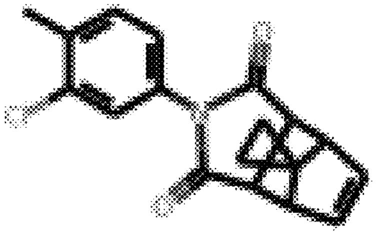
Figure 4H:
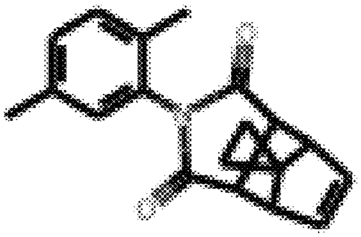
Figure 4I:
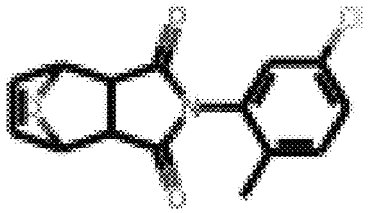
Figure 4J:
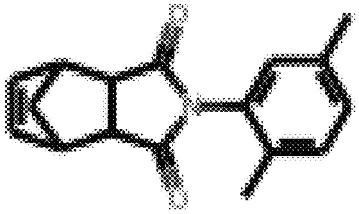
Figure 4K:
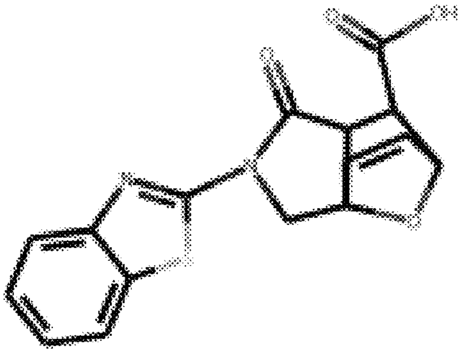
Figure 4L:
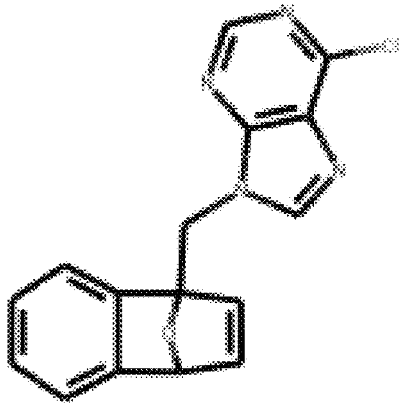
Figure 4M:
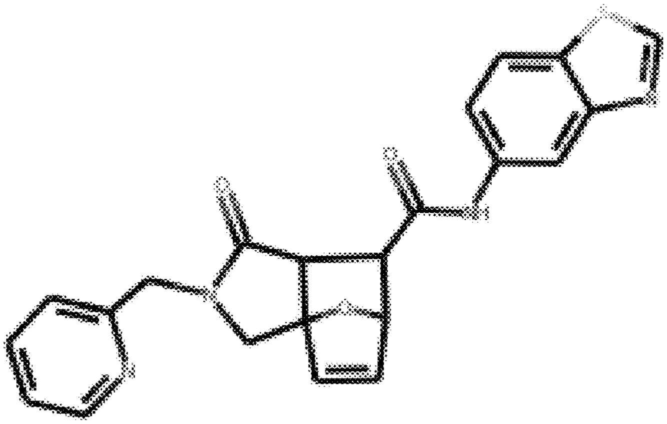
Figure 4N:
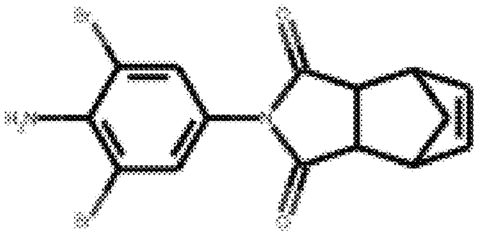
Figure 4O:
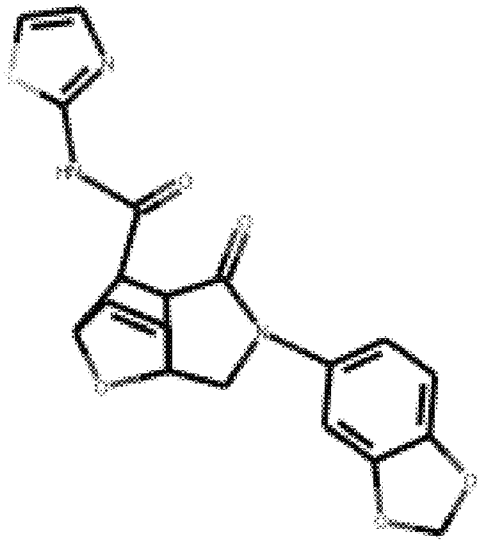
Figure 4P:
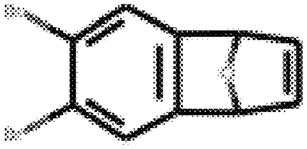
Figure 4Q:
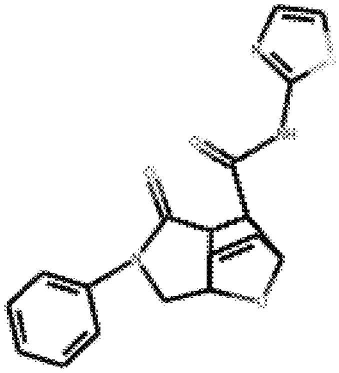
Figure 4R:
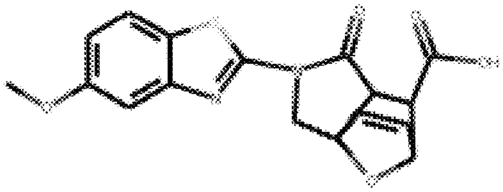
Figure 4S:
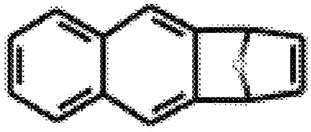
Figure 4T:
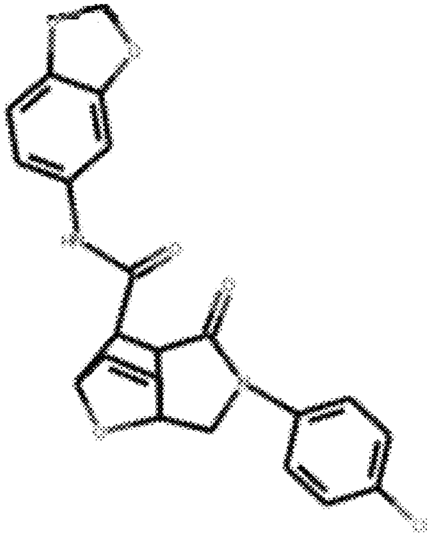
Figure 5A:
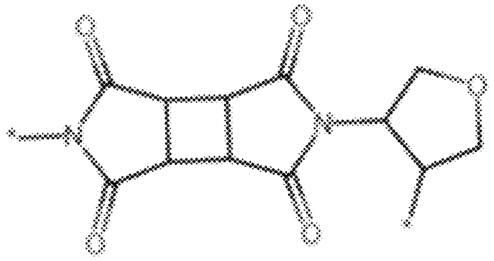
FIGS. 5A-5L provide chemical structures for dielectric polymers, in accordance with an exemplary embodiment of the present invention.
Figure 5B:
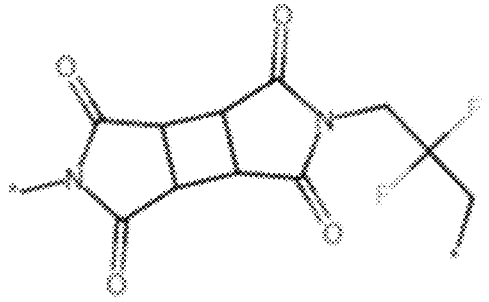
Figure 5C:
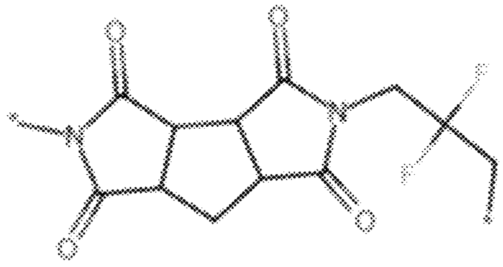
Figure 5D:
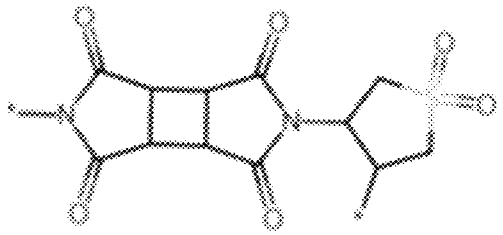
Figure 5E:
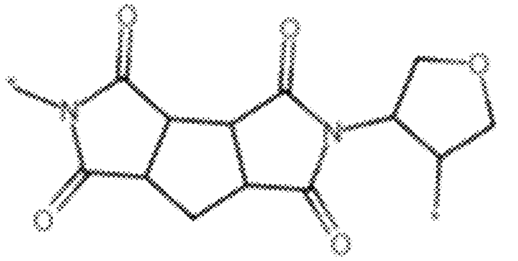
Figure 5F:
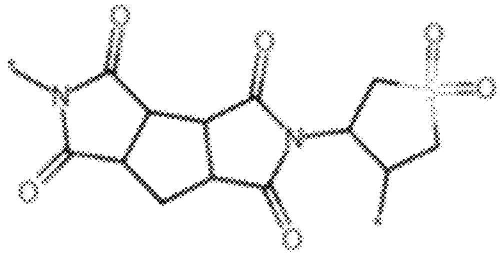
Figure 5G:
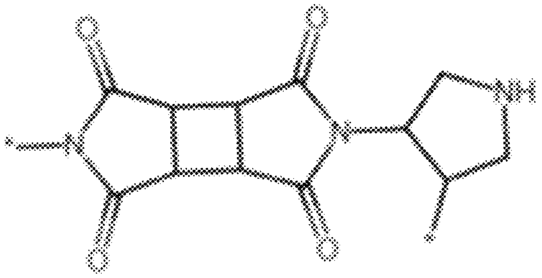
Figure 5H:
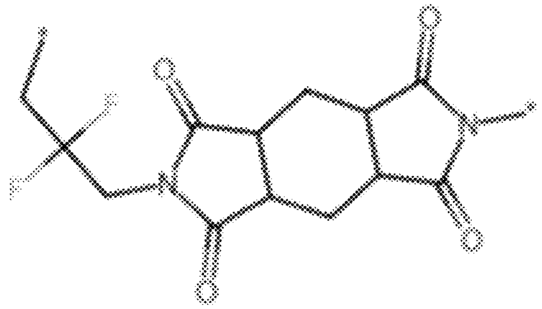
Figure 5I:
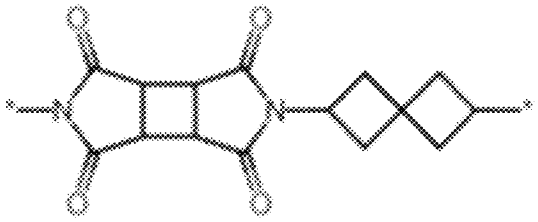
Figure 5J:
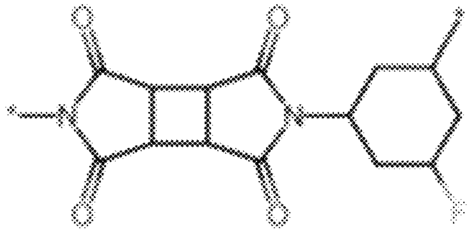
Figure 5K:
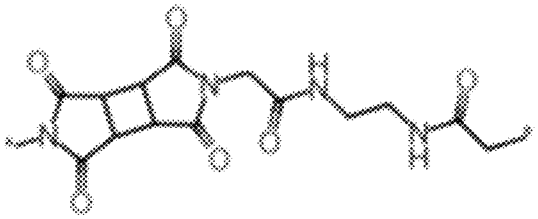
Figure 5L:
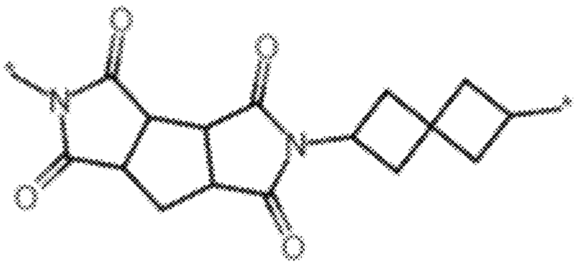
Figure 6A:
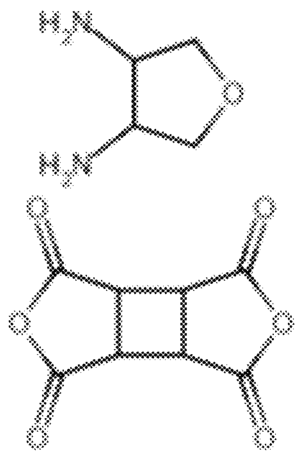
FIGS. 6A-6L provide chemical structures for respective monomers used to the polymers in FIGS. 5A-5L.
Figure 6B:
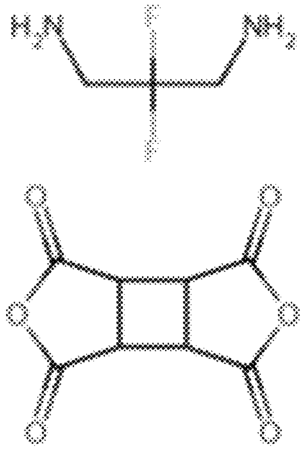
Figure 6C:
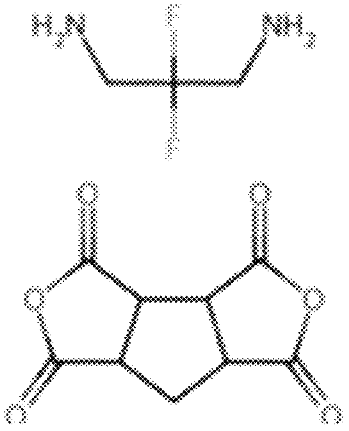
Figure 6D:
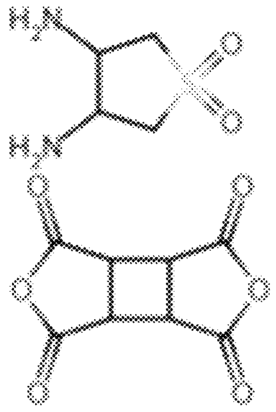
Figure 6E:
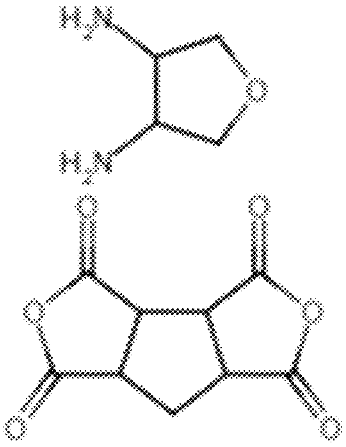
Figure 6F:
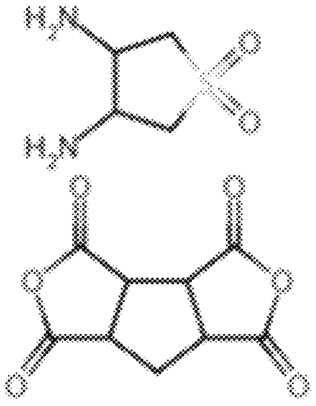
Figure 6G:
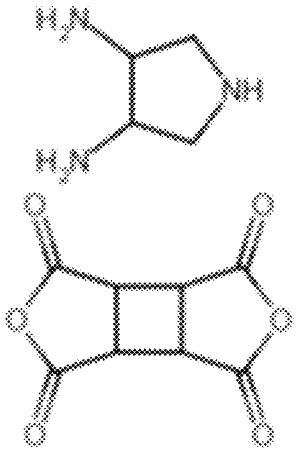
Figure 6H:
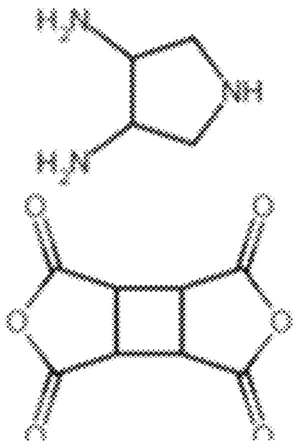
Figure 6I:
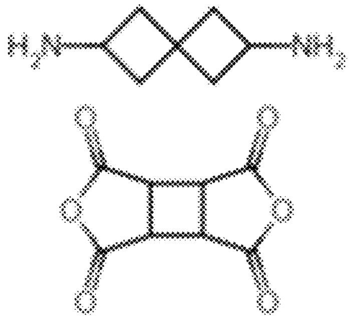
Figure 6J:
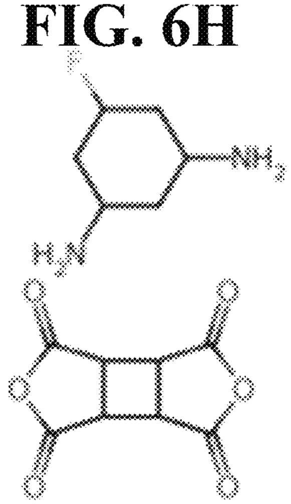
Figure 6K:
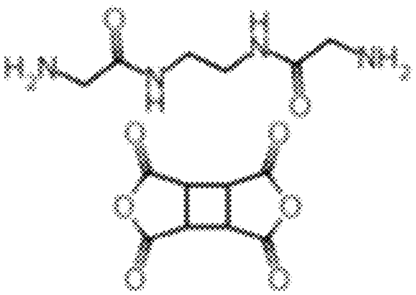
Figure 6L:
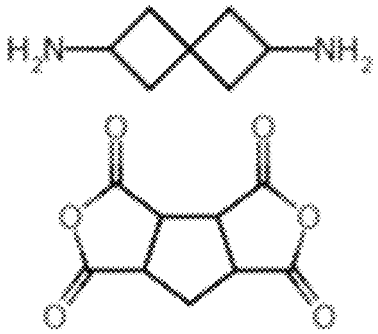

FIGS. 3A-T provide chemical structures for dielectric polymers, in accordance with an exemplary embodiment of the present invention. FIGS. 4A-4T provide chemical structures for respective monomers used to the polymers in FIGS. 3A-3T. That is to say, the structure shown in FIG. 4A is a monomer from which the polymer structure shown in FIG. 3A is formed, and so on for FIG. 3B and FIG. 4B, and so on. FIGS. 5A-5L provide chemical structures for dielectric polymers, in accordance with an exemplary embodiment of the present invention. FIGS. 6A-6L provide chemical structures for respective monomers used to the polymers in FIGS. 5A-5L. That is to say, the structure shown in FIG. 6A is a monomer from which the polymer structure shown in FIG. 5A is formed, and so on for FIG. 5B and FIG. 6B, and so on.

Figure 7A:
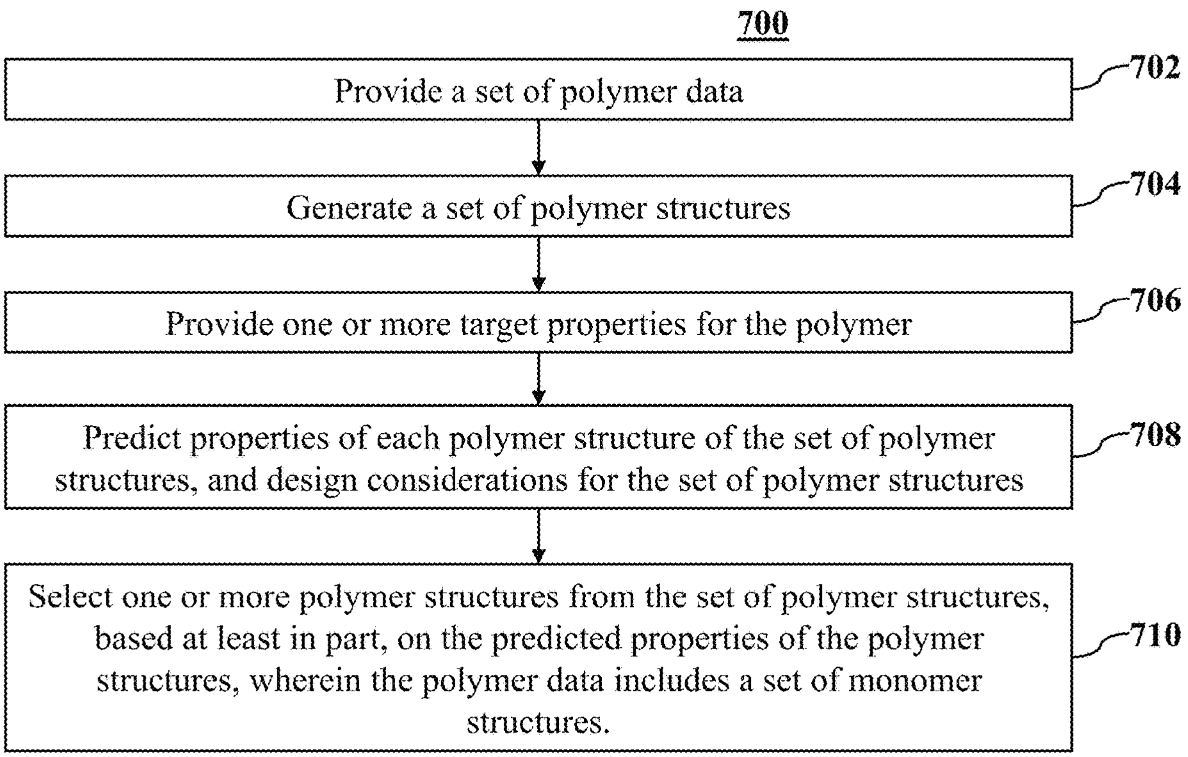
FIGS. 7A-7D provide method flowcharts for a polymer structure design process, in accordance with an exemplary embodiment of the present invention.

Another embodiment of the present disclosure provides a method 700 of designing a polymer. As seen in FIG. 7A, the method 700 can include: providing 702 a set of polymer data; generating 704 a set of polymer structures; providing 706 one or more target properties for the polymer; predicting 708 properties of each polymer structure of the set of polymer structures, and design considerations for the set of polymer structures; and selecting 710 one or more polymer structures from the set of polymer structures, based at least in part, on the predicted properties of the polymer structures. The polymer data can include a set of monomer structures.

Figure 7B:
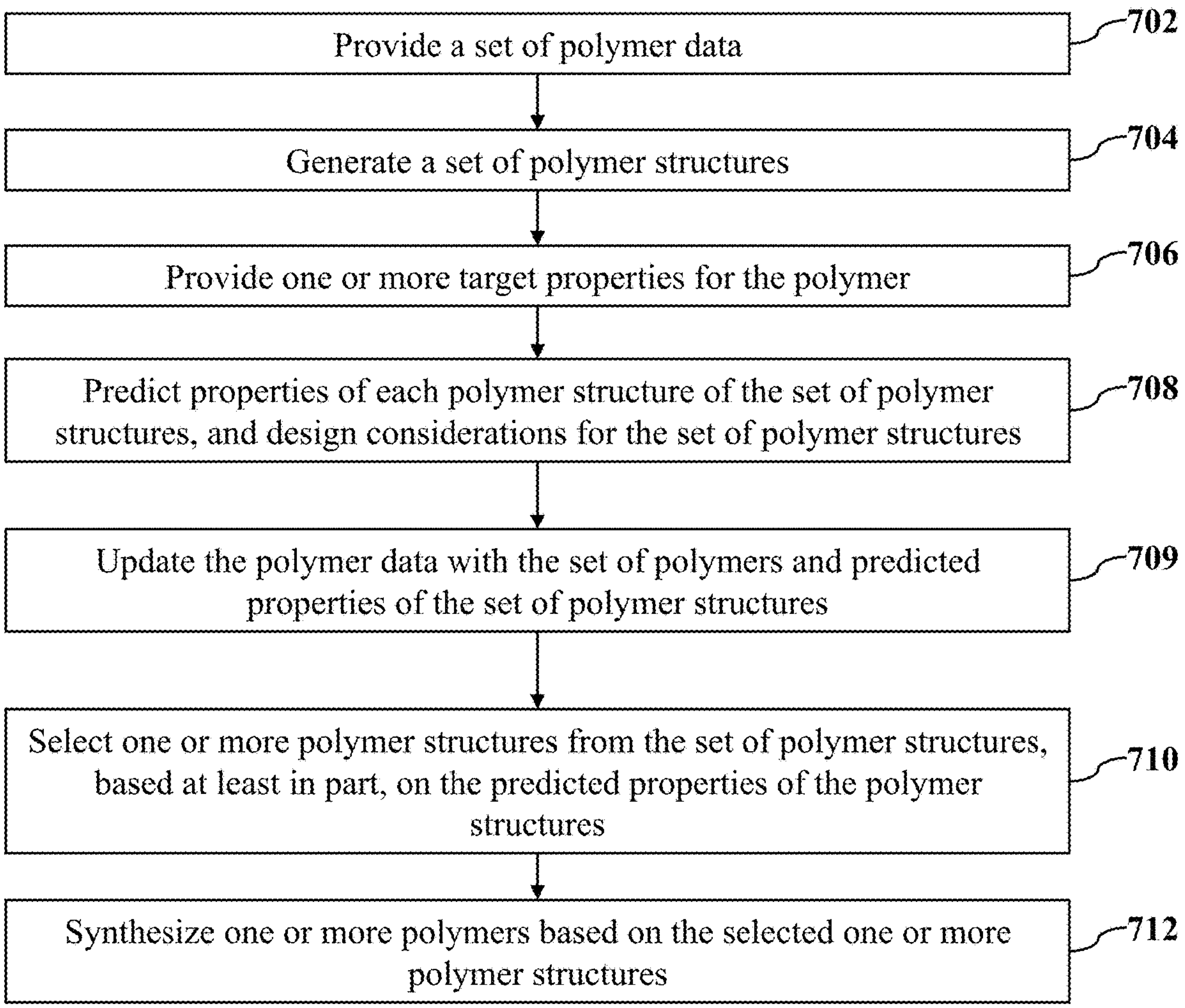

As shown by FIG. 7B, the method 700 further can further include synthesizing 712 one or more polymers based on the selected one or more polymer structures. Providing the set of polymer data can include inputting the polymer data and the one or more target properties into a machine learning model. The method 700 can further include updating 709 the polymer data with the set of polymers and predicted properties of the set of polymer structures.

Figure 7C:
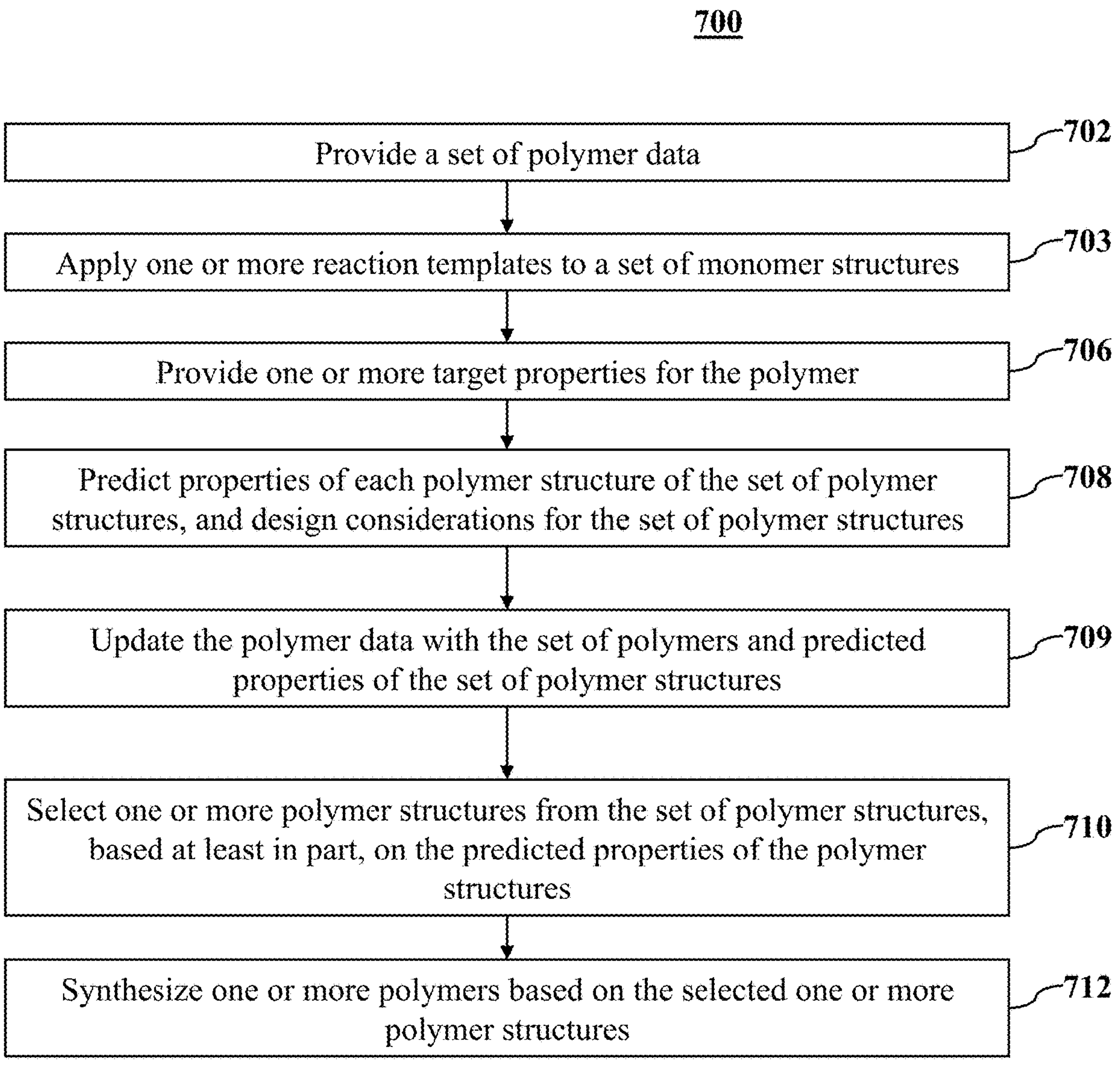

As shown in FIG. 7C, generating the set of polymer structures can include applying 703 one or more reaction templates to the set of monomer structures. The one or more reaction templates can include one or more of: an amide condensation, an ester condensation, an ether condensation, an imide condensation, a double nucleophilic aromatic substitution, a ring opening metathesis, and a click-chemistry based reaction template.

Figure 7D:
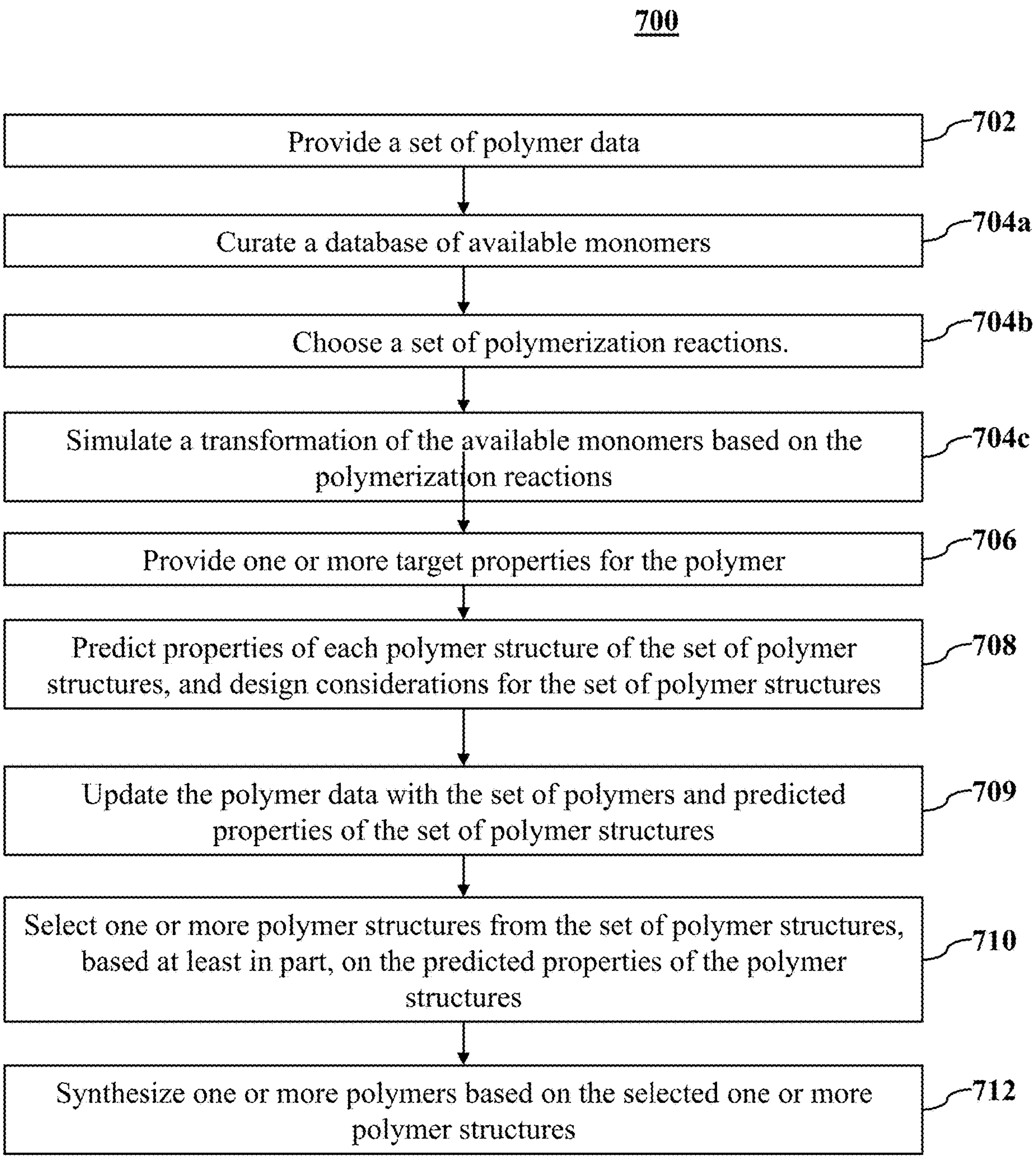

As shown in the embodiment in FIG. 7D, generating the set of polymer structures can include curating 704*a* a database of available monomers and choosing 704*b* a set of polymerization reactions. Generating the set of polymer structures can further include simulating 704*c* a transformation of the available monomers based on the polymerization reactions.

In any of the embodiments disclosed herein, the one or more target properties can include one or more of melting temperature, decomposition temperature, thermal conductivity, band gap, clectron affinity, ionization energy, and solubility.

In any of the embodiments disclosed herein, the polymer data can include computational data and experimental data for a plurality of known polymers.

Figure 22:
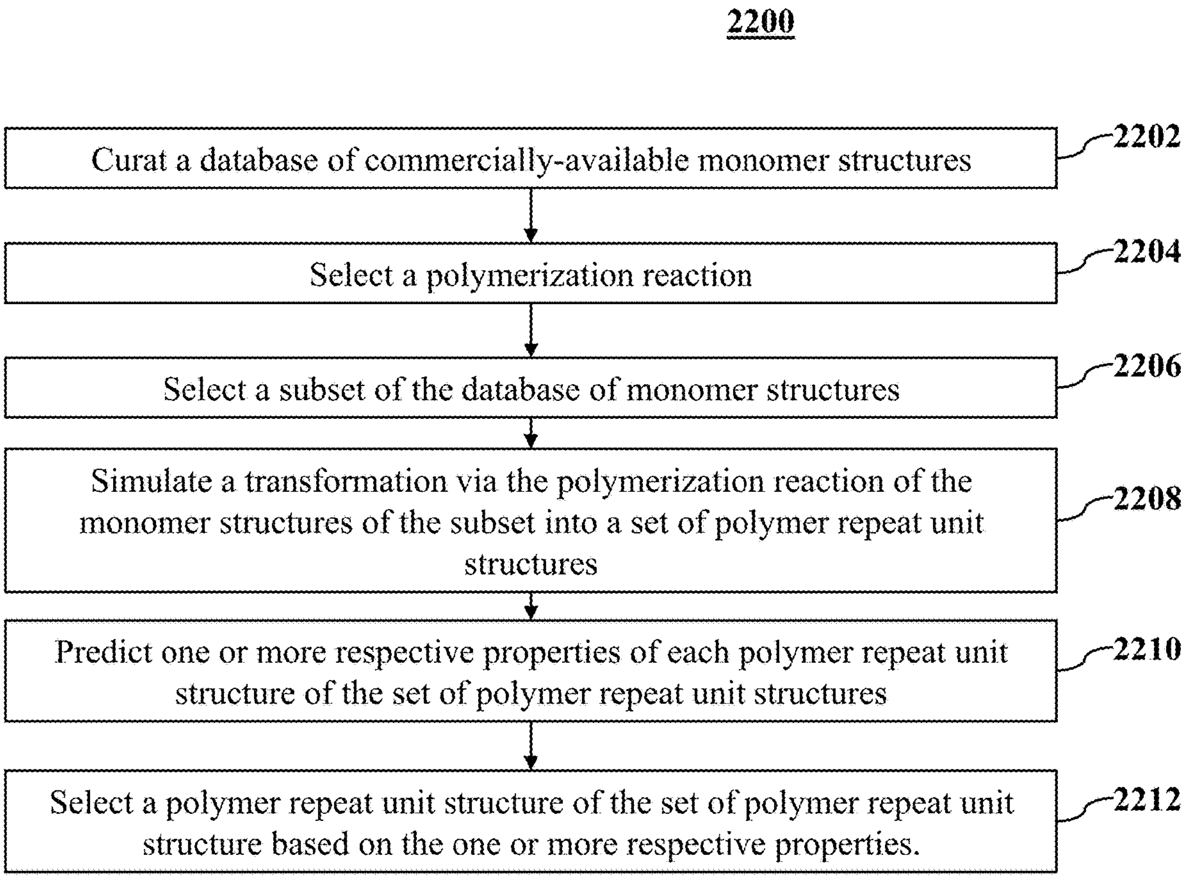
FIG. 22 provides a flowchart for a polymer structure design process in accordance with an exemplary embodiment of the present invention.

FIG. 22 provides a method 2200 of generating a structure for a polymer. The method 2200 can include curating 2202 a database of commercially-available monomer structures; selecting 2204 a polymerization reaction; selecting 2206 a subset of the database of monomer structures; simulating 2208 a transformation via the polymerization reaction of the monomer structures of the subset into a set of polymer repeat unit structures; predicting 2210 one or more respective properties of each polymer repeat unit structure of the set of polymer repeat unit structures; and selecting 2212 a polymer repeat unit structure of the set of polymer repeat unit structure based on the one or more respective properties.

Disclosed herein are polymers that have ultra-high energy density at high temperatures using Artificial Intelligence (AI) based algorithms. Moreover, these algorithms can yield polymer recommendations that are easy to synthesize in the real world. The designs have been validated experimentally. Among them, one polymer has gone through extensive characterization and breakdown studies and displays record-breaking performance.

The following provides some context for the unprecedented nature of this discovery: The current industry standard for high energy density applications is biaxially oriented polypropylene, which shows an energy density of 5 J/cc at 25 °C, and significantly degrades above 25 °C. (and unusable above 100 °C). The new materials disclosed herein, however, can display an energy density of at least 9 J/cc at 200 °C. Additionally, the algorithms disclosed herein have also made many other polymer recommendations. The polymer discussed above serves as a validated exemplar of what is possible with these AI algorithms. Disclosed herein is the workflow used, and a selected list of polymers designed for this important application space.

A method of searching for new dielectric polymers can involve solving the inverse problem and/or solving the forward problem. With the inverse problem, for example, AI algorithms (e.g., GA, VAE, polyG2G) can be used to go from target properties to polymers. But with this, there is little inherent guidance on synthesis, so retrosynthesis could be tried. With the forward problem, a list of known polymers could be generated, properties of those polymers could be predicted using AI methods, and polymers could be screened for those that look promising. But this is limited in size and has no guarantee of success. With the forward problem, synthesizable molecules could be combined using known chemical reactions (virtual synthesis) and billions of synthesizable candidates can be produced. These candidates can be screened and selected. It is this last method that presents a new major opportunity and is pursued herein.

Another embodiment of the present disclosure provides a method of synthesizing a dielectric polymer, the method comprising: providing a set of polymer data; providing one or more target properties for the dielectric polymer; inputting the polymer data and the one or more target properties into an artificial intelligence algorithm to generate a set of polymers, predicted properties of the set of polymers, and design considerations for the set of polymers; selecting one or more polymers from the set of polymers, based at least in part, on the predicted properties of the set of polymers; and synthesizing the selected one or more polymers using an artificial intelligence aided system.

In any of the embodiments disclosed herein, the method can further comprise updating the polymer data with the set of polymers and predicted properties of the set of polymers.

In any of the embodiments disclosed herein, the polymer data can comprise computational data and experimental data for a plurality of known polymers.

In any of the embodiments disclosed herein, the artificial intelligence algorithm can use a deep learning neural network.

In any of the embodiments disclosed herein, selecting the one or more polymers can comprise analyzing the set of polymers through one or more reaction templates.

In any of the embodiments disclosed herein, the one or more reaction templates can comprise an amide condensation, an ester condensation, an ether condensation, an imide condensation, a double nucleophilic aromatic substitution, and a ring opening metathesis.

Another embodiment provides a dielectric polymer. The dielectric polymer can have a structure disclosed in any of the appended drawings.

In any of the embodiments disclosed herein, the dielectric polymer can have a band gap of at least 4 eV, or more preferably at least 4.25 eV.

In any of the embodiments disclosed herein, the dielectric polymer can have a band gap of at between 4.25 eV and 4.5 eV.

In any of the embodiments disclosed herein, the dielectric polymer can have a band gap of at between 4.0 eV and 5.0 eV.

In any of the embodiments disclosed herein, the dielectric polymer can have a glass transition temperature ($T_g$) of at least 200 °C, at least 220 °C, at least 230 °C, or at least 240 °C.

In any of the embodiments disclosed herein, the dielectric polymer can have a $T_g$ of between 200 and 250 °C.

In any of the embodiments disclosed herein, the dielectric polymer can have a dielectric constant of at least 2.5, at least 2.75, at least 2.9, at least 3.0, at least 3.2, or at least 3.3.

In any of the embodiments disclosed herein, the dielectric polymer can have a dielectric constant of 2.5-3.5.

In any of the embodiments disclosed herein, the dielectric polymer can have a dielectric constant of 2.5-3.3.

In any of the embodiments disclosed herein, the dielectric polymer can achieve an energy density of at least 9 J/cc at 200 °C.

In any of the embodiments disclosed herein, the dielectric polymer can achieve an energy density of 9 J/cc at 200 °C.

EXAMPLES

AI-Assisted Discovery of High-Temperature Dielectrics for Energy Storage: energy density, the metric of merit for electrostatic capacitors, is primarily determined by the choice of dielectric material. Most industry-grade polymer dielectrics are flexible polyolefins or rigid aromatics. These polymers possess high energy density or high thermal stability, but not both. In these examples, advanced AI techniques, established polymer chemistry, and molecular engineering are used to discover a suite of dielectrics in the polynorbornene and polyimide families. Many of the discovered dielectrics have high thermal stability and high energy density over a broad temperature range. One of them exhibits a record-setting energy density of 8.3 J/cc at 200 °C. This is approximately 11 times greater than that of any commercially available polymer dielectric. By incorporating oxygen into the polymer backbone, a sizable increase in energy density of over 5.5 J/cc at 200 C was observed. Additionally, position and identity of the phenyl substituents modulate the energy density by nearly 1 J/cc. These polymers widen the scope of potential applications for electrostatic capacitors within the 85-200° Ctemperature range, at which there is presently no good commercial solution. More broadly, these examples demonstrate the impact of AI on chemical structure generation and property prediction, highlighting the potential for materials design advancement beyond electrostatic capacitors.

Electrostatic capacitors are critical energy storage components in advanced electrical systems in the defense, aerospace, energy, and transportation sectors. Compared with other, more vigorously discussed, energy storage devices—such as batteries, fuel cells and supercapacitors—electrostatic capacitors offer unparalleled power density (107 W/kg). This attribute renders electrostatic capacitors particularly advantageous for deployment in diverse fields, including wind pitch control (with maximum temperatures around 125 °C), hybrid, all-electric and rail vehicles (150 °C), pulsed power systems (180 °C), aircraft and aircraft launchers (300 °C), and space exploration (480 °C). An existing challenge, however, is to significantly enhance the energy density ($U_e$)—particularly at high temperatures—of electrostatic capacitors, thereby unlocking substantial space and weight saving. For example, direct current bus capacitors in power inverters of hybrid vehicles can take up more than 23% of the total weight and 35% of the overall volume. Cooling systems, essential to maintain the stability of temperature-intolerant dielectrics, further exacerbate the space and volume constraints.

Figure 8A:
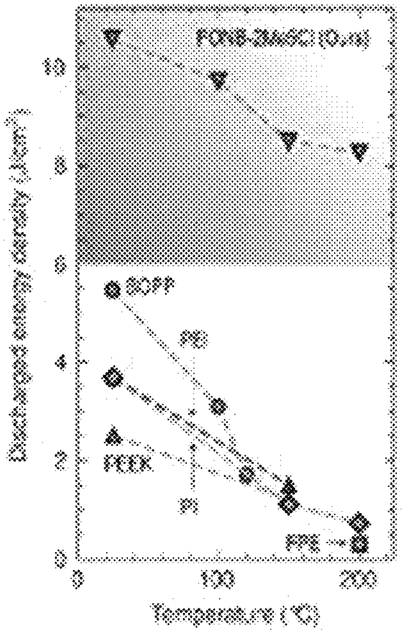
FIG. 8A provides a plot of temperature versus discharged energy density for existing polymers and one polymer disclosed herein, in accordance with an exemplary embodiment of the present invention.
Figure 8B:
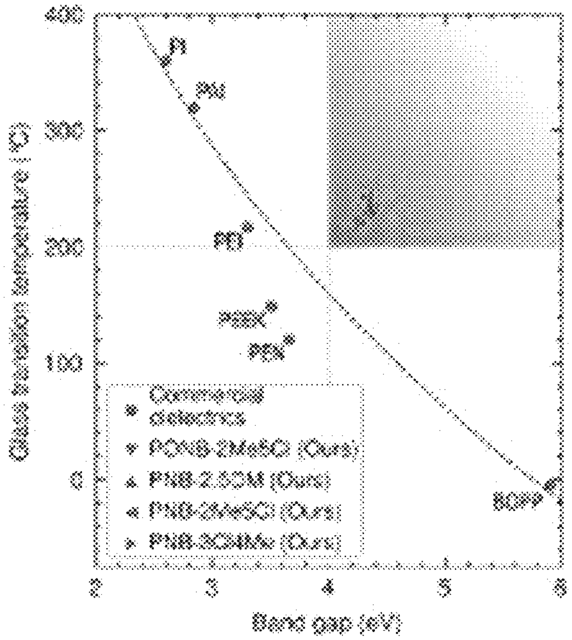
FIG. 8B provides a plot of band gap versus glass transition temperature for existing polymers and various polymers disclosed herein, in accordance with an exemplary embodiment of the present invention.
Figure 8C:
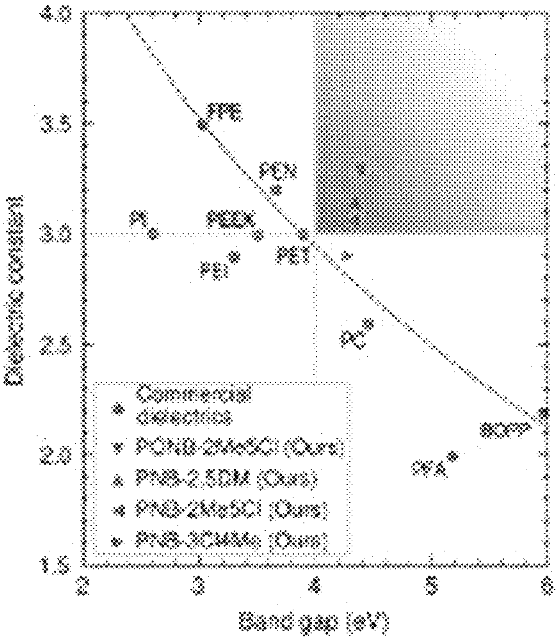
FIG. 8C provides a plot of band gap versus dielectric constant for existing polymers and various polymers disclosed herein, in accordance with an exemplary embodiment of the present invention.
Figure 8D:
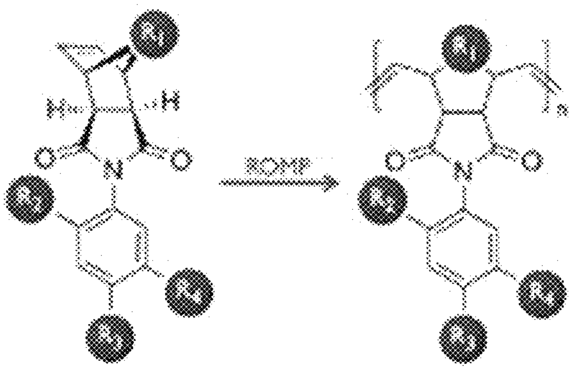
FIG. 8D provides the synthetic path and chemical structure of four exemplary dielectric polymers, in accordance with an exemplary embodiment of the present invention.

FIGS. 8A-8C relate to filling the dielectric void in commercially available materials. FIG. 8A shows that a new polymer, PONB-2Me5Cl, surpasses current state-of-the-art commercial dielectric materials, especially at elevated temperatures. FIGS. 8B-8C show that the high performance of this polymer is related to an improved combination of $T_g$, electronic band gap ($E_g$) and permittivity ($\epsilon$) compared to commercial polymers. FIG. 8D shows the chemical structure of PONB-2Me5Cl and three other polymers discovered in this work. The trend lines in FIG. 8B and FIG. 8C are logarithmic fits to {PI, BOPP, PAI, PEI} and {FPE, BOPP, PEN, PET, PC}, respectively. Table 1 shows names of the polymers used in these examples and their structures in relation to the generic structure of FIG. 8D only. It is important to note that $R_1$-$R_3$ as referenced in Table 1 are not necessarily in the same position as the $R_x$ designators in other figures (such as FIGS. 1A-1F) discussed herein. In this EXAMPLES section, unless otherwise specifically stated, all positions $R_x$ refer to those in FIG. 8D. However, the structures described in Table 1 and FIG. 8D are the same as some other structures discussed herein.

TABLE 1

| Name | $R_1$ | $R_2$ | $R_3$ |
|---|---|---|---|
| PONB-2Me5Cl | —O— | —Me | —Cl |
| PNB-2Me5Cl | —C— | —Me | —Cl |
| PNB-3Cl4Me | —C— | —H | —Cl |
| PNB-2,5DM | —C— | —Me | —Me |

Today's high-power capacitors use biaxially oriented polypropylene (BOPP) as the dielectric, a material that has served well for over three decades and one on which the community, industry, and supply chain have heavily invested in. BOPP and similar polyolefins possess low dielectric loss and a large ($E_g$) due, in part, to the absence of π-stacking moieties. However, these polymers also have a low dielectric constant $\epsilon$ and poor mechanical stability at elevated temperatures, both attributes correlated to the lack of π-π stacking. The interplay of these various factors results in a situation where BOPP maintains sufficient $U_e$ at room temperature but then rapidly degrades with increasing temperature, as shown in FIG. 1*a*.

Commercial alternatives to BOPP with high thermal stability have been explored. However, these polymers trade stability for low $E_g$ and, consequently, a low $U_e$ (see PI, PEEK, PEI, FPE in FIG. 8A). Additional features are expected of these materials, as discussed in subsequent sections, exposing the tightrope (FIG. 8B-C) that must be walked to craft new, functional polymer dielectrics that can meet the demands of modern and future technologies.

To a large extent, the function of a polymer is governed by its underlying chemistry. The number of variations that can be produced by chemical permutations in a single polymer is staggering. For instance, derivatizing styrene alone through arene functionalization can lead to 1014 possibilities, as discussed in more detail below. Within the vast expanse of chemical possibilities for all polymers, it is likely that a wide variety of high-performance dielectrics await discovery. Well-trained and calibrated AI, capable of handling large numbers, can help converge on extraordinary or "outlier" materials rapidly. During the past decade, this powerful approach has guided the discovery, chemical synthesis, and physical characterization of materials across domains, including polymer dielectrics with high energy density up to 100 °C.

Figure 9A:
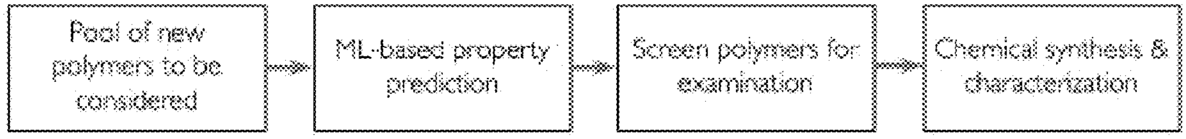
FIG. 9A provides a flowchart for a method for synthesizing polymers, in accordance with an exemplary embodiment of the present invention.

Disclosed herein is a previously unknown polynorbornene dielectric, named PONB-2Me5Cl (see FIG. 8D), with unprecedented $U_e$ over a broad range of temperatures. At 200 °C as shown in FIG. 8A, the polymer has an unprecedented $U_e$ of 8.3 J/cc-over an order of magnitude higher than that of any commercial alternative. PONB-2Me5Cl was discovered in silico using an AI protocol for chemical structure optimization disclosed herein, and then subsequently synthesized and characterized. This AI protocol is illustrated in FIG. 9A and discussed below, demonstrates a robust pathway for the creation of synthetically accessible polymer designs meeting stringent property and performance targets. The protocol begins with the chemical structure generation step, a process composed of multiple substeps described in FIG. 9B. First, well-known polymerization reactions are digitized. Then, a set of available monomers are curated. Finally, the reactions are applied to the monomers, yielding a hypothetical polymer library that fills gaps in uncharted but synthetically amenable regions of the chemical space. This automated virtual structure generation process encodes selected key principles, so that their wisdom can be captured and applied at scale. Upon generating a set of chemical structures, machine-learned structure-property models are used to screen the set for candidates predicted to meet each materials property requirement FIG. 9C and FIG. 10. The entire optimization protocol, from chemical structure generation up to chemical synthesis, is termed polyVERSE—"polymers designed by Virtually-Executed Rule-Based Synthesis Experiments".

In addition, disclosed herein are other new polymer design advancements to be considered in the future. These include modified versions of PONB-2Me5Cl (achieved through R-group engineering or the incorporation of nanofillers or coatings) and novel polyimides, which are prioritized based on existing functional high-temperature polymers. These new designs display potential for boosted high temperature $U_e$ and reduced loss, while also allowing for synthesis using "green" solvents. "Green" as used herein means, generally, environmentally friendly.

AI-assisted dielectric design: for use in high temperature applications, the dielectrics in capacitors must be stable at extreme operating temperatures (e.g., they must have a high $T_g$) while simultaneously exhibiting a high $U_e$. The maximum $U_e$ of an electrostatic capacitor using a linear dielectric is determined by the dielectric's breakdown field ($E_{bd}$) and its $\epsilon$.

$$U_e = \frac{1}{2}\varepsilon_0 \varepsilon E_{bd}^2 \quad \text{Equation 1}$$

where $\varepsilon_0$ is the vacuum permittivity.

Due to the intricate nature of dielectric breakdown mechanisms in polymers, direct simulations of engineering breakdown under realistic conditions are impractical (although the intrinsic breakdown of perfect, defect-free, crystalline systems can be handled. A pragmatic alternative approach is to include a positively correlated proxy such as $E_g$ during the design process. In summary, a polymer with a high $T_g$ (e.g., >100 K), large $E_g$ (>4 eV), and high $\epsilon$ (>3) is likely to exhibit a high $U_e$ at high temperatures.

Regrettably, simultaneous achievement of all three property requirements is beyond the capabilities of available polymers. polyVERSE is a three-step formalization of the problem, including chemical structure generation, property prediction, and screening steps. In the first step, polymer structures are derived from small molecules using established chemical reactions. As a result, the requisite monomer(s) and polymerization reaction for any generated polymer are determined. This advantage is absent from the majority of prior work on polymer chemical structure generation, where reaction chemistry is not explicitly encoded, resulting in a large fraction of structures that lack easily identifiable monomers and reactions.

Figure 9B:
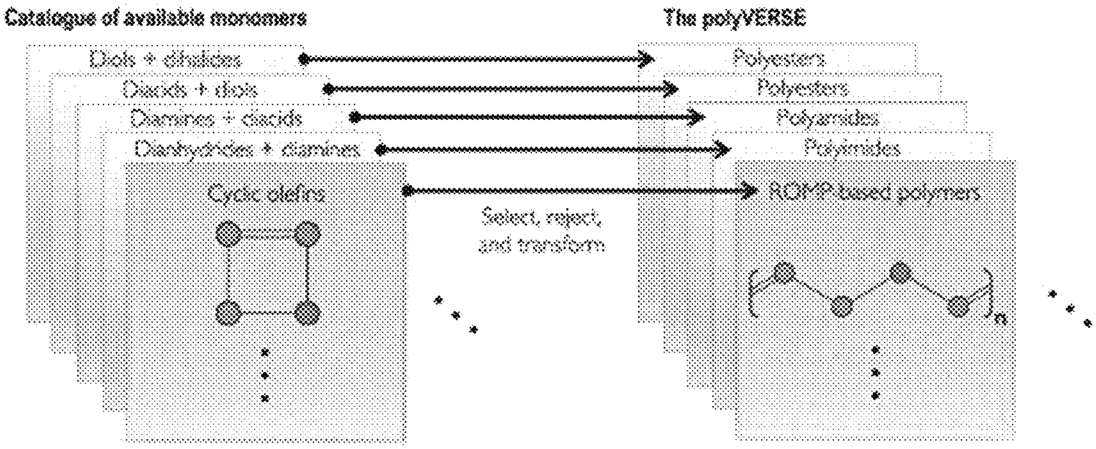
FIG. 9B provides a flowchart for generating polymer structures, in accordance with an exemplary embodiment of the present invention.
Figure 9C:
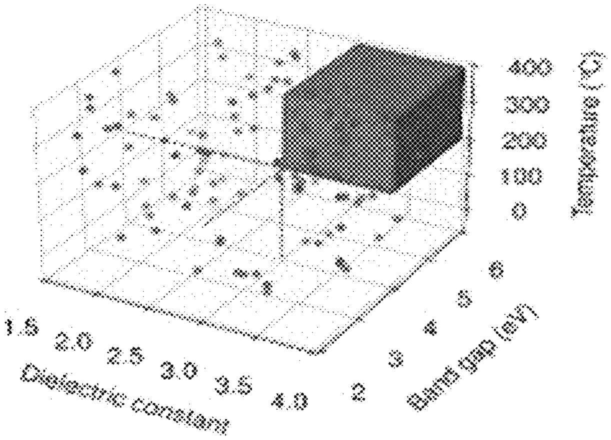
FIG. 9C provides a graphical representation of a structure-property screening, in accordance with an exemplary embodiment of the present invention.
Figure 10:
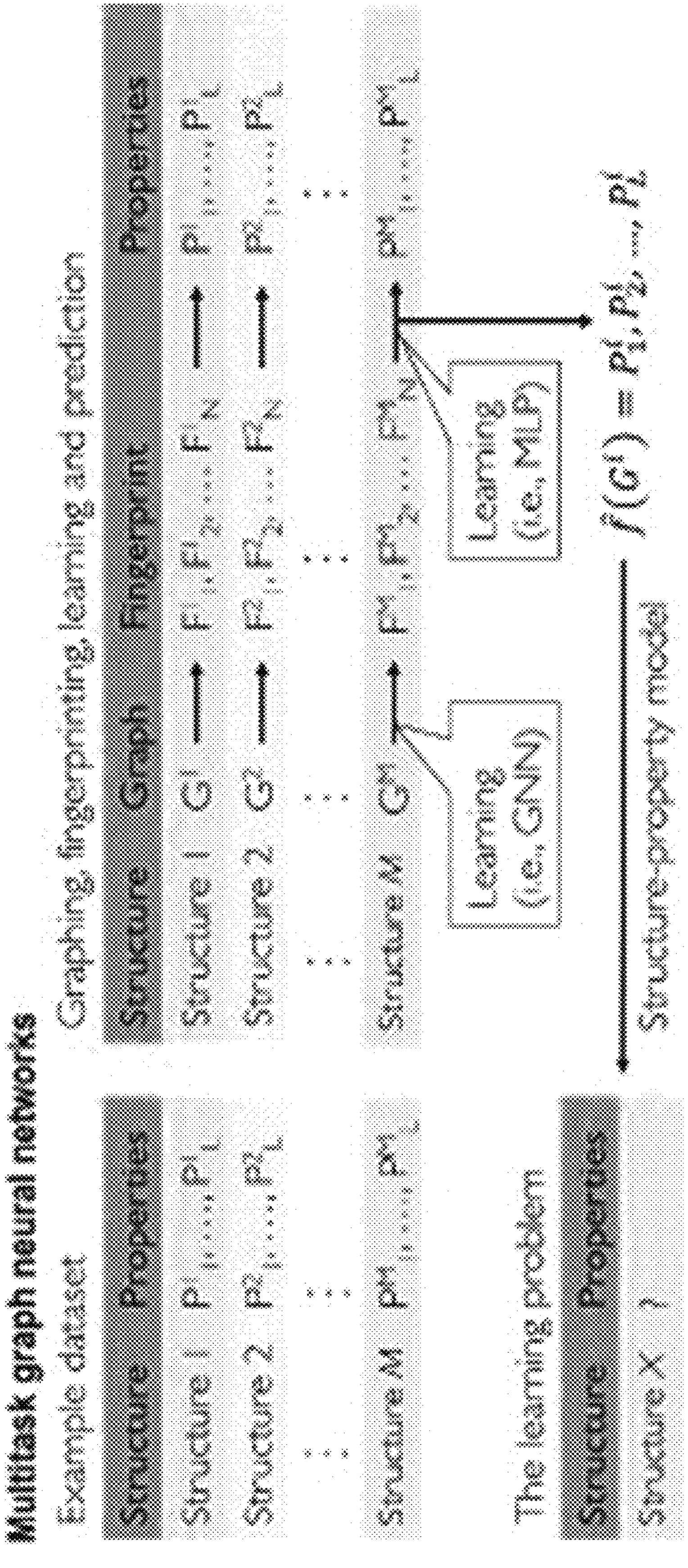
FIG. 10 provides a graphical representation of a machine learning process, in accordance with an exemplary embodiment of the present invention.

FIG. 9A-10 depict AI-assisted design of polymers for energy storage. FIG. 9A—the present design approach consists of four high-level steps. First, generate a pool of chemical structures to choose from. Then, predict the properties of each. Next, use the predicted properties to screen for the best candidates which, finally, are synthesized and characterized. FIG. 9B shows how polymer repeat unit chemical structures are generated in three steps. First, a master database of available monomers is curated. Then, a polymerization reaction is chosen. For that reaction, a subset of monomers is selected on the basis of established chemical rules, others are rejected. Finally, the selected monomers are chemically-transformed from a monomer into a polymer repeat unit. As shown in FIG. 10, structure-property models are trained using multitask graph neural networks. The starting point is an example dataset containing labeled pairs of the form [Structure, Properties]. Then, each chemical structure is converted to a machine-readable graph, with heavy atoms as nodes and covalent bonds as edges. A model is trained on the data to establish a mapping between a structure's graph and cach property. An intermediate output, also learned during training, is the fingerprint. Properties are predicted for each chemical structure in the polyVERSE database. FIG. 9C shows screening performed using a sequence of carefully chosen, application-specific, filters: high $T_g$, $E_g$ and $\epsilon$. Each filter functions as a discerning sieve, sequentially honing in on increasingly attractive chemical structures for high-$U_e$, high-temperature applications. Structures with the best predicted properties are selected for synthesis.

It is important to consider certain constraints when dealing with polymer reactions to increase the likelihood of high molecular weight products. The methodology disclosed herein stands out by addressing these constraints during the structure generation process. Another difference is that this example method relies on commercially available monomers. These pragmatic choices are aimed at increasing the probability of synthetic amenability of the proposed chemical structures.

The starting point of poly VERSE is a set of small molecules derived from the databases ZINC15 and ChEMBL. The tranche of small molecules selected from the ZINC15 database included those that were readily purchasable and with standard reactivity. Filters were applied to strip counterions and chirality. Finally, SAscore was used to remove complex molecules, whittling the dataset down to ≈8 million unique "Available monomers".

The next component of the chemical structure generation process is a growing set of handcrafted reaction templates, one per polymerization reaction. Each template contains a set of transformations (i.e., bond-breaking and -forming events) and a set of monomer classifiers. In AABB-type polycondensation, a polymer is formed through repeated reactions between so-called AA and BB monomers. This reaction involves two monomers, so the template has two monomer classifiers. FIG. 9B describes how these elements are used to produce novel polymers. First, the monomer classifiers are used to select and reject monomers from the "Available monomers". Then, the selected monomer(s) undergo the transformation(s), forming a product—a polymer repeat unit—that is deposited in the polyVERSE database.

As a first pass, polymers that can be formed by ring-opening metathesis polymerization (ROMP) were focused on since this class contains polymers with the best reported high-temperature $U_e$ to date. The ROMP template contains one chemical transformation, i.e., cleavage at the reactive site's double bond, depicted in FIG. 8D. The template also contains one monomer classifier, since ROMP can proceed using just a single type of cyclic olefin. To begin with, the classifier checks if a given molecule is a cyclic olefin. The remaining decision boundaries drawn by the classifier are motivated by structure-property models. For simplicity, the models assume perfectly repeating polymers with infinite molecular weight. Because chemical reactions are inherently stochastic, perfect recurrence of the repeating unit along each polymer chain is not always practical. However, this approximation is realistic for polymers with narrow reaction pathways. Thus, the present classifier only accepts molecules with one cyclic olefin group. Although infinite molecular weight is also not possible in practice, the approximation becomes more apt as the molecular weight of a polymer increases. Thus, this classifier only accepts molecules with olefin-containing rings of 3-5 atoms or 7-11 atoms. Rings of 6 or 12+ atoms usually are not sufficiently strained to drive the polymerization reaction to high conversion, resulting in low molecular weight chains. Additionally, molecules with strong electrophilic groups (e.g., halides, acyl halides, carbonyls, and carboxyls) adjacent to the cyclic olefin group are discarded due to their tendency to reduce or distribute the ring strain.

Another crucial component of polyVERSE is described, namely, the mechanism used to model the relationship between structure and properties. In this work, the properties of interest are $T_g$, $E_g$, and f. Establishing a direct connection by hand between a polymer's chemical structure and any of these properties is highly nontrivial. Instead, data and machine-learning (ML) are used to learn three structure-property models, one each for the aforementioned properties. It is noted that, while $T_g$ and $E_g$ may be modeled with high accuracy using only the chemical structure as input, f can exhibit a strong dependence on temperature and frequency, in addition to chemistry. Therefore, ML predictions of f at 100 Hz and room temperature $$(f_{100}^{RT})$$

are focused on herein. Each of the three models is trained on relatively large data sets using the Polymer Graph Neural Network (polyGNN) algorithm. In polyGNN, a polymer is reduced to its repeat unit. This repeat unit is then converted to a graph with atoms as nodes and chemical bonds as edges. On a randomly chosen test set, the models achieved good accuracy, with a root-mean-square error of 32 °C for $T_g$, 0.5 for $$(f_{100}^{RT}),$$

and 0.5 eV for $E_g$.

In total, 28,428 ROMP-based polymer chemical structures were generated from the set of "Available monomers" using this template. This list was screened for structures with exceptional ML-predicted properties: $T_g$>100 °C $$(f_{100}^{RT}) > 3,$$

and $E_g$>4 eV. Next, the remaining structures were rank-ordered according to the product of their predicted properties $$T_g \times (f_{100}^{RT}) \times E_g.$$

Finally, five of the top twelve candidate structures were selected as synthetic targets on the basis of raw materials cost and expert evaluation of synthesizability.

Energy storage performance: of the five candidates, high molecular weight samples of PONB-2Me5Cl, PNB-2,5dimethyl (PNB-2,5DM), PNB-2Me5Cl, and PNB-3C14Me (see FIG. 8D and FIGS. 1A-1F for the chemical structure of the various polymers) were prepared using ROMP and cast into films. Polymerization of the fifth polymer was unsuccessful. The resulting films were characterized with differential scanning calorimetry (DSC) to determine $T_g$, spectrometry to determine $E_g$, and spectroscopy to determine f as a function of temperature and frequency. In general, there is a close agreement between these ML predictions and experimental measurements. The mean absolute prediction error for the four polymers was 12 °C. (or 5% in mean absolute percentage error) for $T_g$, 0.4 eV (8%) for $E_g$, and 0.7 (22%) for $$(f_{100}^{RT}).$$

Figure 13A:
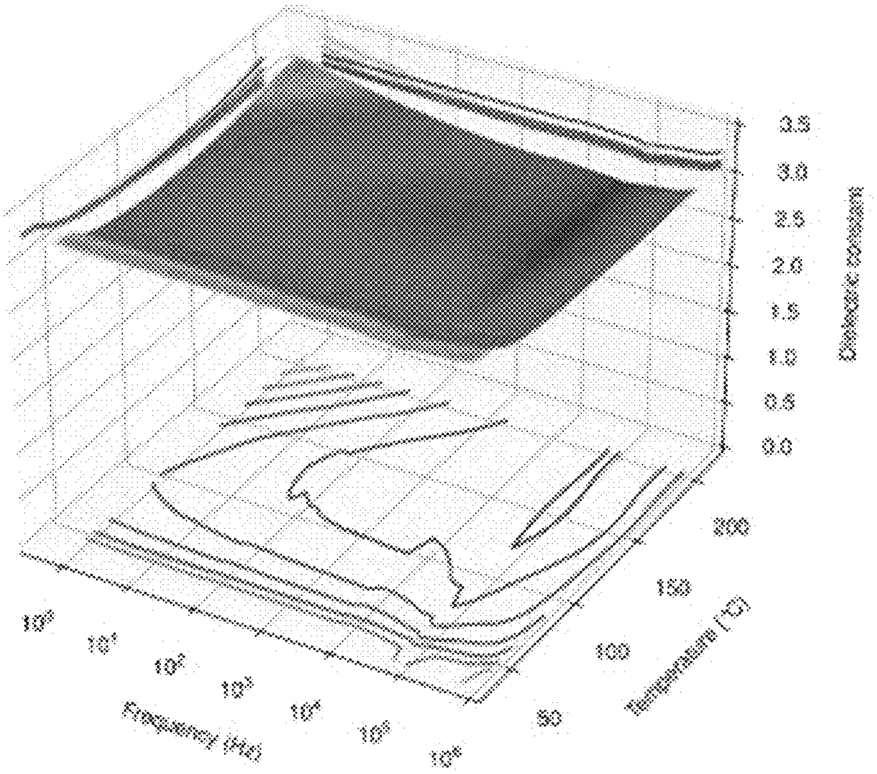
FIG. 13A provides a graphical representation of dielectric constant versus temperature and frequency for a dielectric polymer disclosed herein, in accordance with an exemplary embodiment of the present invention.

As predicted by the present ML models and depicted in FIGS. 8B-8C, each of the newly discovered dielectrics breaks out of the inverse $T_g$-$E_g$ and f-$E_g$ relationships exhibited by commercial polymers. The high $T_g$ of each film ensures mechanical robustness at high temperatures. PONB-2Me5Cl has the highest $E_g$ (4.4 eV) of the group of films. The high $E_g$ acts as a substantial barrier to electron conduction, leading to an unprecedented $E_{bd}$ (>800 MV/m at 100 °C and 750 MV/m at 200 °C, see FIG. 11A). This property is complemented by a moderate, thermally-stable dielectric constant (see FIG. 13A). The combination, extraordinary $E_{bd}$ and moderate f, results in elevated $U_e$ maintained from room temperature to 200 °C. It is emphasized in particular that PONB-2Me5Cl possesses a $U_e$ of 8.3 J/cc at 200 °C.—a best reported $U_e$ value that is 11 times that of any commercial polymer at this temperature—potentially eliminating the need to consume energy and space with cooling systems in demanding applications such as wind pitch control, hybrid, electric and rail vehicles, and pulsed power systems.

Figure 11A:
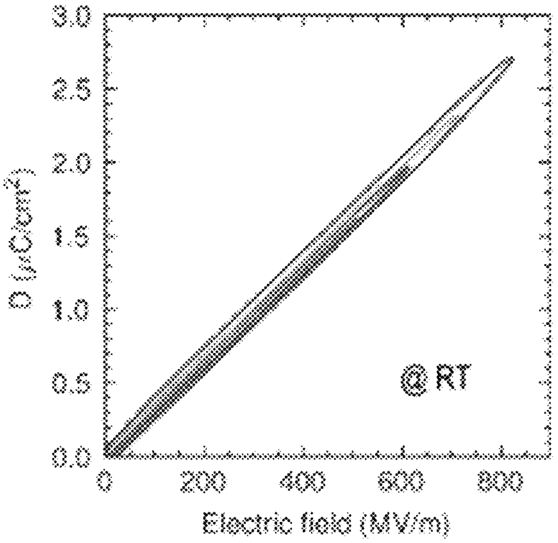
FIGS. 11A-11D provide plots showing displacement-electric field loops for an exemplary dielectric polymer at room temperature, 100 C, 150 C, and 200 C, respectively, in accordance with an exemplary embodiment of the present invention.
Figure 11B:
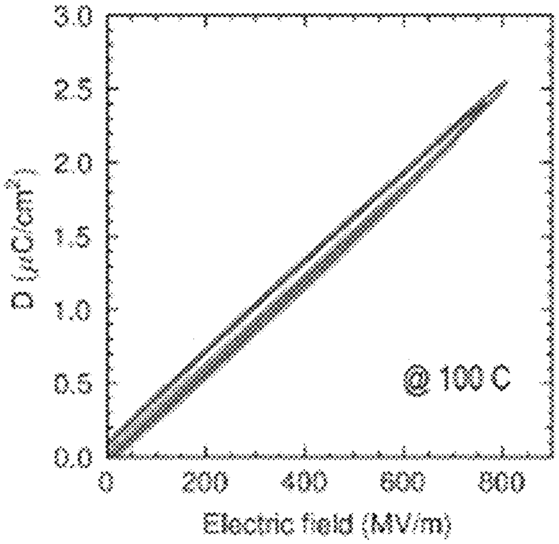
Figure 11C:
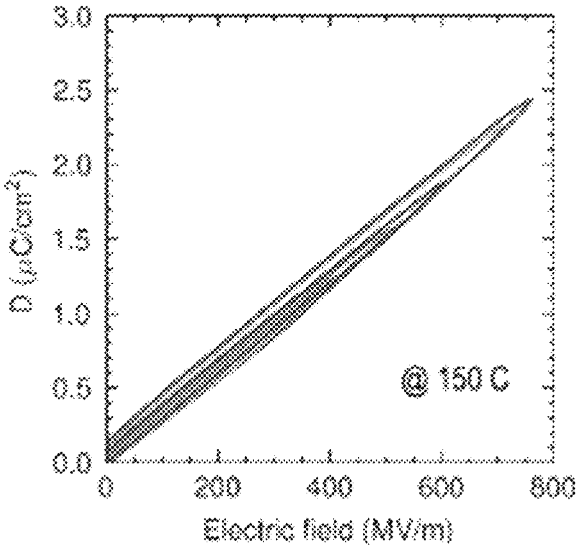
Figure 11D:
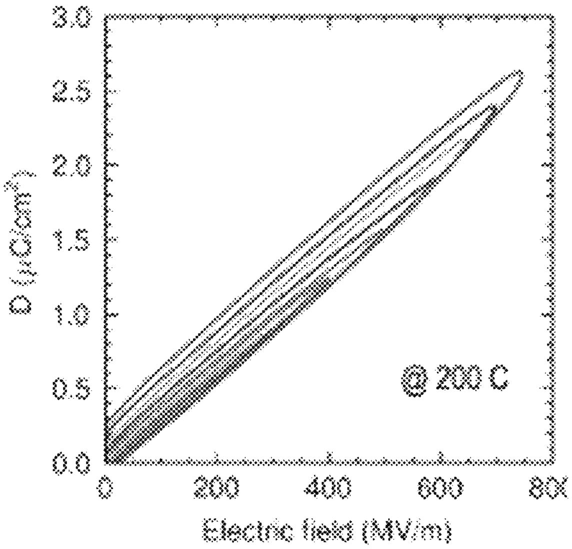
Figure 12:
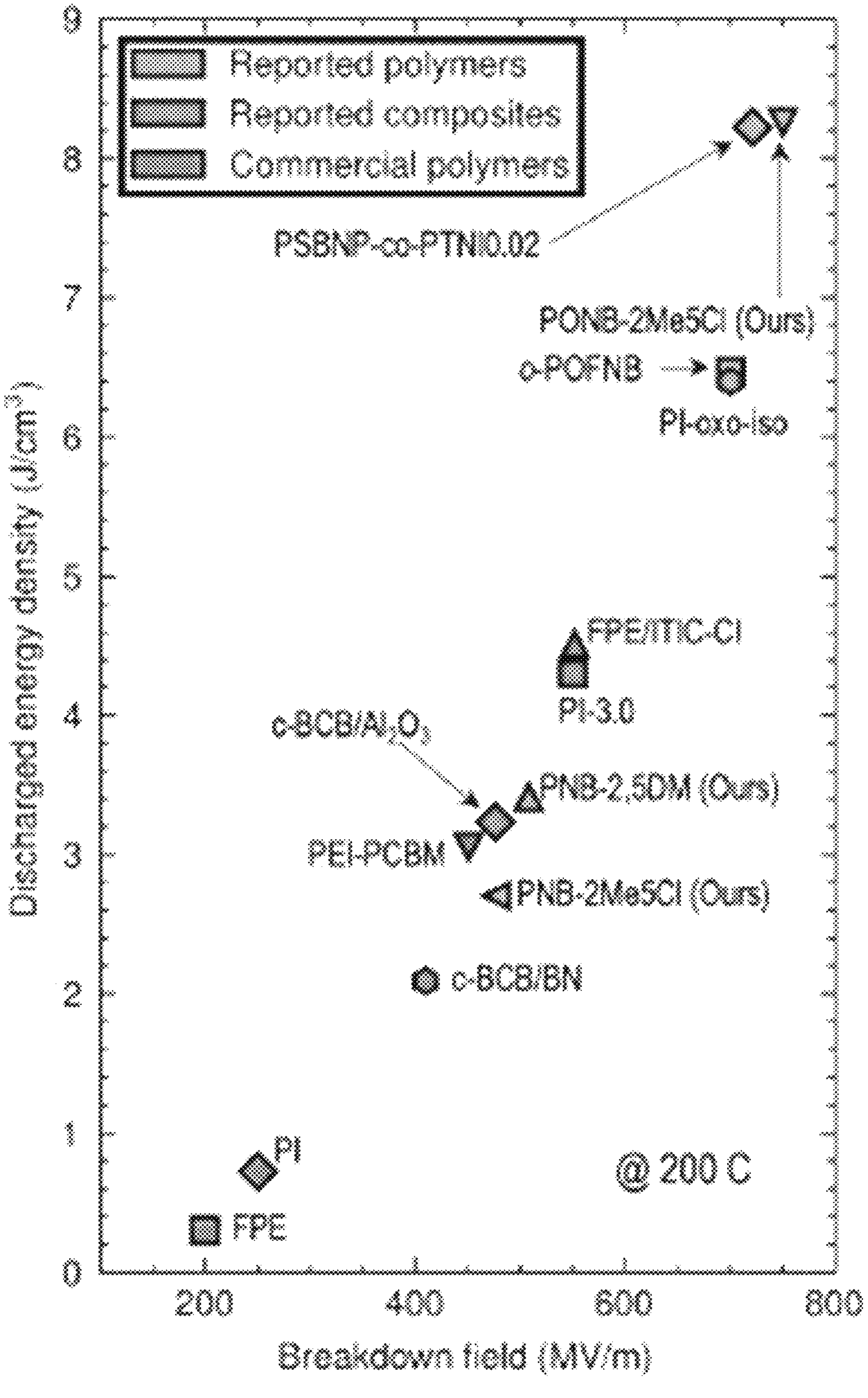
FIG. 12 provides a plot showing discharged energy density versus breakdown field for commercial polymer and select polymers disclosed herein, in accordance with an exemplary embodiment of the present invention.

FIG. 11A-12 Breakdown field and energy storage performance. FIG. 11A shows displacement-electric field (D-E) loops for PONB-2Me5Cl at four temperatures (including room temperature, RT). FIG. 11B shows discharged energy density vs. breakdown field at 200 °C for notable commercial and reported polymer-based dielectrics.

Figure 13B:
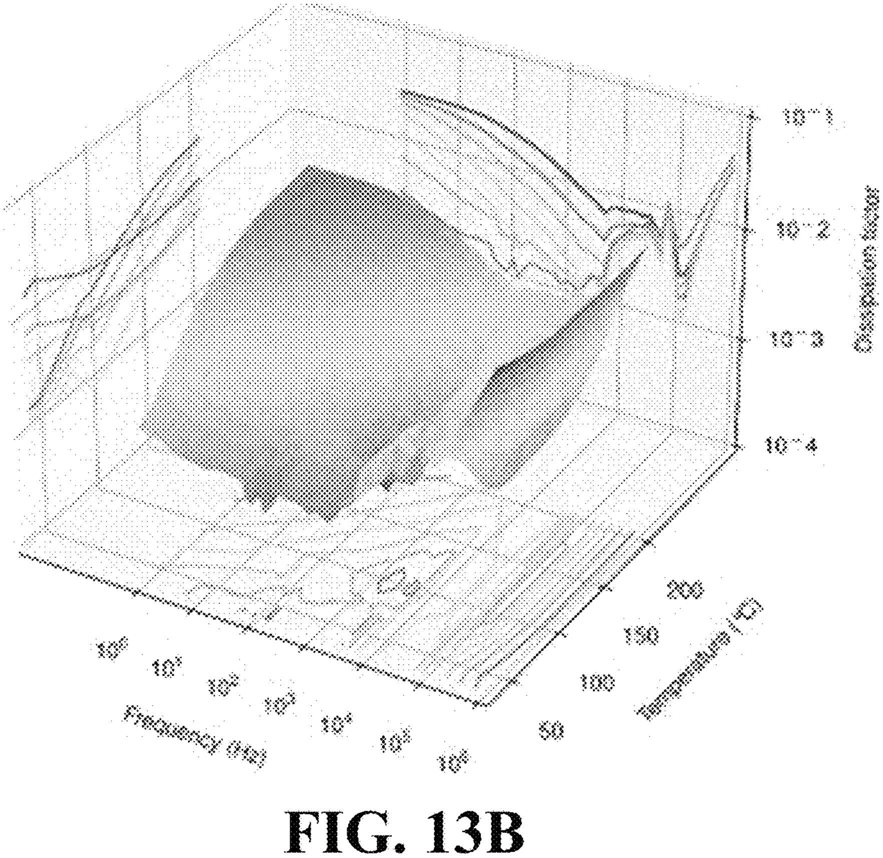
FIG. 13B provides a graphical representations of dissipation factor versus temperature and frequency for a dielectric polymer disclosed herein, in accordance with an exemplary embodiment of the present invention.

The performance of PONB-2Me5Cl may be understood by contrasting its chemical structure with that of other polymers. For example, PONB-2Me5Cl possesses bicyclic rings and double bonds that stiffen the backbone, while its pendant phenyl ring impedes rotation around the chain axis. These structural features endow PONB-2Me5Cl with a $T_g$ significantly higher than that of saturated hydrocarbons like BOPP. Thus, PONB-2Me5Cl remains stable at high temperatures, while BOPP completely breaks down below 125 °C. Second, PONB-2Me5Cl contains several π systems per repeat unit while BOPP is completely devoid of such features. As a result, the $E_g$ of BOPP is over 1.5 eV higher than that of PONB-2Me5Cl. Despite this, BOPP's $E_{bd}$ at room temperature is lower than that of PONB-2Me5Cl (750 MV/m compared with 825 MV/m, as shown in FIGS. 11A-11D). This suggests that breakdown in BOPP involves more than just electronic factors; thermal and/or electromechanical effects may also contribute. Third, the presence of π systems and polar groups (e.g., C═O), raises the ϵ of PONB-2Me5Cl above BOPP while maintaining a reasonable dielectric loss (see FIG. 13B).

Although significant strides have been made that explain the interplay between chemical structure and energy storage performance, the present disclosure reveals other unresolved aspects. First, it is observed that while PNB-2Me5Cl and PNB-2,5DM differ only in the chemical identity of one aryl substituent $R_4$, this slight difference alters $E_{bd}$ by approximately 30 MV/m and $U_e$ by about 0.7 J/cc at 200 °C. (FIG. 12). Even more impactful is the backbone chemistry. PNB-2Me5Cl and PONB-2Me5Cl are identical except for $R_1$, yet PONB-2Me5Cl possesses increased $E_g$ and ϵ, leading to a striking escalation at 200 °C in $E_{bd}$ and $U_e$ of almost 300 MV/m and over 5.5 J/cc, respectively (FIG. 12).

While not yet fully understood, these subtle chemical tweaks can be utilized to design higher-performing polynorbornenes. For example, a straightforward hypothesis is that PONB-2,5DM—containing oxygen at $R_1$ and methyl groups at $R_2$ and $R_4$—would possess a higher $U_e$ than any of the polymers studied here. Interestingly, the polyVERSE database currently lacks PONB-2,5DM—despite its chemical similarity to the other polymers—due to the absence of its corresponding monomer in the ZINC database version used in these examples.

Dielectric constant and dissipation factor—the dielectric constant (see FIG. 13A) and dissipation factor (see FIG. 13B) of PONB-2Me5Cl as a function of frequency and temperature. Contour plots are displayed on the walls of each diagram.

"Greener" pastures: it is appropriate to evaluate and contextualize the environmental impact of the materials proposed in this work. A few key aspects, including lightweighting and chemical synthesis, are highlighted in this section. A lighter vehicle requires less energy to move, resulting in improved fuel efficiency and lower greenhouse gas emissions. Historically, this objective has driven the adoption of lighter load-bearing materials like aluminum, carbon fiber, and plastics. Additional savings may be realized by economizing the capacitor, which can account for over 20% of a vehicle's weight. As a practical example, each dielectric in FIG. 12 eliminates the need for heavy capacitor cooling systems up to 200 °C. Among these, those with higher $U_e$ are preferred, as this attribute reduces the amount of capacitor material required to store a given amount of energy. Regarding this matter, PONB-2Me5Cl shows a large improvement over traditional polymers (e.g., FPE and PI). Further gains are possible; in special cases, the $U_e$ and thermal stability of traditional polymers has been boosted by incorporation of semiconducting nanofillers. The efficacy of this strategy with respect to PONB-2Me5Cl is left to future work.

Each synthesis step typically requires energy inputs, raw materials (some of which may be derived from natural resources, such as petroleum-based feedstocks), and generates waste (some hazardous). Therefore, from an ecological perspective, shorter synthetic pathways are often preferred. In terms of PONB-2Me5Cl, fair comparisons are o-POFNB and PSBNP-co-PTNI0.02, two recently discovered polymers with high $E_{bd}$ and $U_e$ at 200 °C. (scc FIG. 12). Each polymer also happens to be synthesized by ROMP. PONB-2Me5Cl is synthesized from starting materials in a three-step procedure, two steps to prepare the monomer and one for polymerization. The number of steps is identical for o-POFNB. PSBNP-co-PTNI0.02, meanwhile, is a binary copolymer, synthesized in six steps total. One monomer is synthesized from commercially available starting materials in a four-step procedure and the other in a one-step procedure. In the final step, the two monomers are copolymerized. PI-oxo-iso is another polymer that displays an energy density near that of PONB-2Me5Cl, o-POFNB, and PSBNP-co-PTNI0.02 at 200 °C. Overall, these comparisons suggest that the environmental profile of PONB-2Me5Cl is on par with, or better than, the limited group of known polymers in its class.

Along with short synthetic pathways, raw materials—such as solvents—with low impact are desired. Solvents are used in high volumes, including in the production of synthetic polymers, which amounts to 30 million tons annually. Thus, the search for "green solvent"—compatible polymers has intensified. The dielectrics discovered in this work were polymerized in dimethylacetamide (DMAc) and tetrahydrofuran (THF)—solvents that are decidedly not "green". Traditionally, a solvent is defined as "green" only if its environmental, health, and safety (EHS) impacts are low and the resources required to produce the solvent are sustainable. The importance of these criteria is well documented. In 1989, as part of the Montreal protocol, carbon tetrachloride was banned for its contribution to ozone layer depletion. According to the 2015 World Health Organization IARC evaluations, chloroform and dichloromethane are likely to be carcinogenic to humans. Meanwhile, the current production of many solvents, especially hydrocarbons, is dependent on petroleum derivatives.

Attempts to enumerate and weight different EHS and sustainability criteria have led to an array of "green" solvent lists. The lists come from different organizations (pharmaceutical companies, societies, academia, and collaborations between these groups), exhibit different goals (identification of classical, commercially-available "green" solvents vs. identification of novel "green" solvents not yet on the market), and thus offer different conclusions.

In this section, the two "greenest" solvents, water and ethanol, are analyzed. Both solvents have a "recommended" EHS profile and are sustainable, with water being a renewable resource and ethanol being derived from biomass at an industrial scale. While the solubility of o-POFNB and PSBNP-co-PTNI0.02 in water and ethanol has not been reported, PONB-2Me5Cl, is insoluble in both. Additionally, the polymer is not soluble in 1-butanol, and is only partially soluble in ethyl acetate, the next two "greenest" solvents. Motivated by these findings, a polyGNN model was trained on 26,884 data points to predict the room temperature solubility of a given polymer in 61 solvents, including water and ethanol. Combining this Solvent polyGNN with the previously trained triad of polyGNN models, the polyVERSE was screened for polymers predicted to be soluble in water or ethanol while also maintaining good high temperature dielectric properties—$T_g$>200 °C, $$\in_{100}^{RT} > 3,$$

and $E_g$>4 eV.

The initial polyVERSE database, containing only the ROMP-based structures, yielded zero hits meeting all four criteria. Attention was then turned to the polyimide family, which contains a handful of commercially available polymer dielectrics (e.g., Kapton®, Ultem®, SIXEF-44®, Perflouro polyimide, Upilex-S®) with high $T_g$. Polyimides are synthesized in two steps. First, the condensation of a dianhyride and diamine yields a polyamic acid prepolymer. Finally, the amic acid groups on the prepolymer are converted to imide groups, commonly by heat treatment. A handful of polyamic acids and polyimides have been reported to be soluble or partially soluble in water or ethanol. Based on these findings, a reaction template for polyimides was crafted. Applying this template to the data set of "Available monomers" yielded 66,103 candidate polyimide structures, which were then deposited into the polyVERSE database. Out of these, a few hundred chemical structures, depicted in FIG. 14, were predicted to meet all four criteria. Those polyimides with the most affordable monomers were selected, narrowing the list to four candidate structures. A proposed synthetic route for each polyimide candidate is given at the right of FIG. 14.

It should be noted that the four selected polyimides exhibit slightly lower predicted $T_g$ values than the four ROMP polymers disclosed herein (204-213 °C vs. 220-243 °C), but significantly higher predicted $E_g$ values (5.4-5.7 eV vs. 4.3-4.4 eV), which implies higher $E_{bd}$ for the polyimides. The high band gap is due, in part, to the absence of aromatic rings in the polyimides. Meanwhile, these polymers can still maintain a relatively high $T_g$ due to an abundance of aliphatic rings. In fact, previously synthesized fully aliphatic polyimides exhibit $T_g$ as high as 423 °C.

Discussion: demonstrated herein is the practical utility of polyVERSE for the high-temperature dielectric application, a problem entailing multiple competing material properties. This approach revealed PONB-2Me5Cl, an exceptional polymer for electrostatic energy storage, especially in high-temperature applications such as wind pitch control, hybrid vehicles and rail, and pulsed power systems. A handful of other prospective dielectrics in the polyVERSE database, including some with "green" profiles, are recommended. Characterization of these previously unknown polymers has also revealed important chemical design rules for high $U_e$ at high temperatures. Considering these outcomes, it is clear that the current iteration of polyVERSE has revealed the potential to design synthesizable, functional polymers.

High-performance fillers or coatings can be added to the PONB-2Me5Cl matrix. Or, by applying the design rules discovered in this work, the chemical structure of the polymer matrix itself may be slightly tweaked. Likewise, rapid expansion of the polyVERSE database—via inclusion of new reaction templates, monomer databases, or both—facilitates the exploration of additional polymer families.

Any of these approaches to materials discovery would benefit from increased accuracy of the polyGNN models—perhaps using strategies like pretraining—to reduce the amount of time spent on bad leads. Moreover, significant resources should be dedicated to a new generation of AI characterized by human interpretability. For example, AI should not merely indicate that substituting a chloroarene with an aryl methyl or replacing a cycloalkane with an alicyclic ether improves the energy storage of a polynorbornene.

Figure 14:
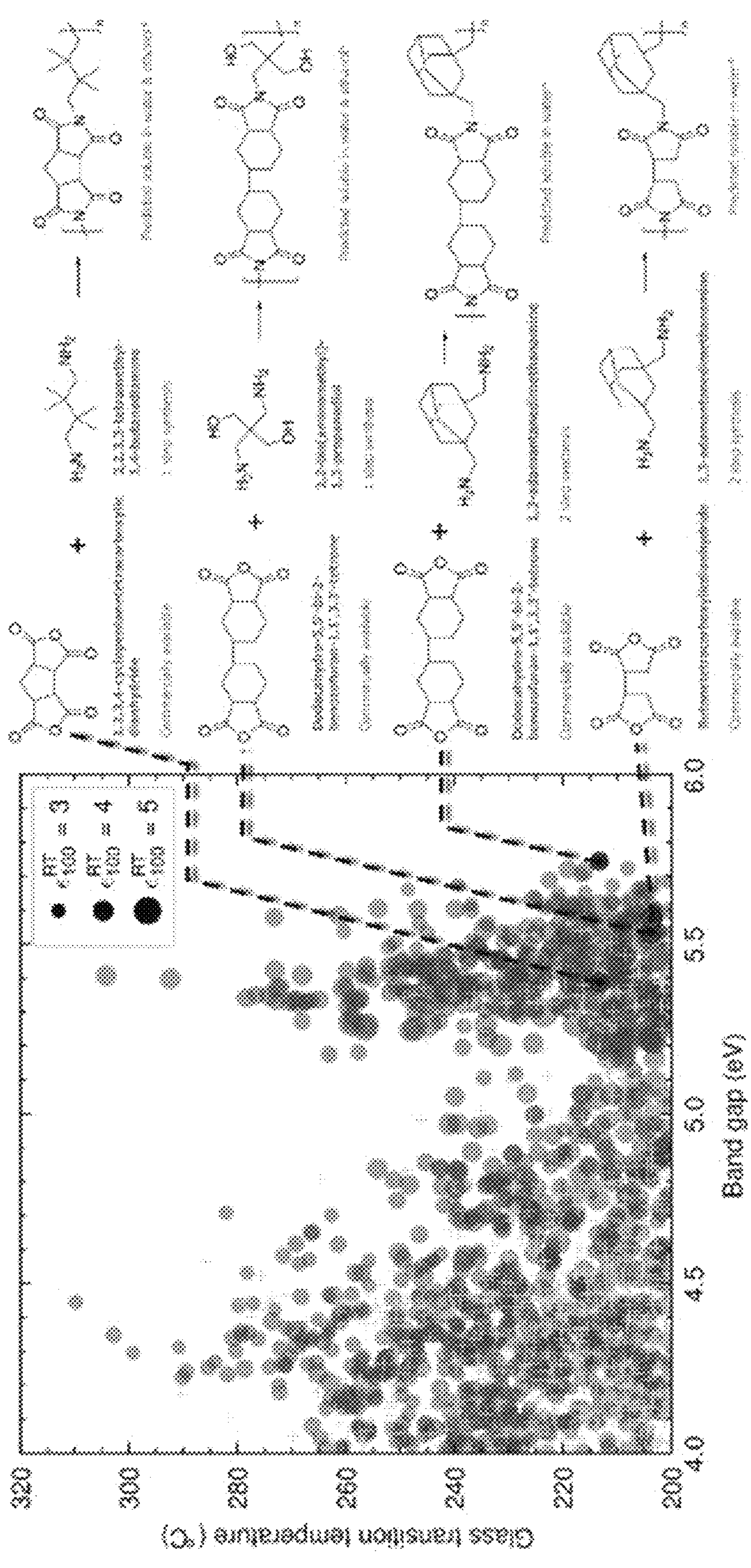
FIG. 14 provides a dot plot of band gap and dielectric constant versus glass transition temperature for various polyimide structures, with exemplary polyimide structures shown traced to their relative position on said plot, in accordance with an exemplary embodiment of the present invention.

FIG. 14 relates to going "green": out of 66,103 polyimide structures, approximately 1,800 are predicted to exhibit $T_g$>200 °C, $$\in \frac{RT}{100} > 3,$$

and $E_g$>4 eV. Roughly half of these chemical structures are predicted to be insoluble in water and/or ethanol (pluses). The others, represented by dots, are predicted to be soluble in water and/or ethanol. Four of these structures with feasible synthetic pathways are proposed. The solubility prediction is performed on the polyamic acid precursor to the polyimide.

Methods and Materials: Anhydrous toluene, THF, methanol, ethanol, acetic anhydride, and anhydrous sodium acetate were purchased from Fisher Scientific. Exo-3,6-epoxy-1,2,3,6-tetrahydrophthalic anhydride (Oxanorbornene anhydride), Dichloromethane Anhydrous, 5-cloro-2-methylaniline, and ethyl vinyl ether were purchased from TCI America. cis-5-Norbornene-exo-2,3-dicarboxylic anhydride, 3-chloro-4-methylaniline, and 2.5-dimethylaniline were purchased from Oakwood Chemical. The Grubbs Generation 2 catalyst was used for ring opening metathesis polymerization and was purchased from Sigma-Aldrich.

A Bruker DMX 500 MHZ Nuclear Magnetic Resonance (NMR) spectrometer was used to confirm the structure and purity of each monomer and polymer. Thermogravimetric analysis (TGA) and differential scanning calorimetry (DSC) were used for the thermal characterization of synthesized polymers. TGA was performed using a TA Instruments TGA Q-500-0188 at a heating rate of 20 °C/min. DSC was performed using a TA Instruments DSC Q20 with a heating and cooling rate of 10 °C/min. The molecular weight of each polymer was determined using the Waters GPC system, where DMAc was used as the mobile phase and polystyrene standards were used. The band gap of each polymer was calculated by performing UV-Vis spectroscopy on a PerkinElmer's Lambda 1050 UV/Vis/NIR spectrometer. Electrical characterization. The dielectric constants and dissipation factors were measured using the commercial dielectric spectroscopy instrument Solartron SI 1260 with the dielectric interface Solartron 1296. Measurement temperature was controlled by placing the sample in the oven Delta Design 9015. A 15 mm gold/palladium film, serving as the electrode, was coated on both sides of each dielectric film. High-field D¬E loop measurements were carried out using a developed Sawyer-Tower polarization loop tester by applying a half-sinusoidal voltage with a frequency of 100 Hz, while measuring the polarization current through the film. The high voltage amplifier Trek Model 10/40 was used in the system to apply a voltage with a maximum amplitude of 10 kV. For D-E loop measurement, gold/palladium was coated on both sides of the film as electrodes with a diameter of 3 mm by the sputter coating method.

polyVERSE polyimides were generated using two monomer classifiers, and a set of chemical transformations. One classifier looked for suitable diamines and the other for suitable dianhydrides. Both classifiers require the presence of exactly two functional group, each with similar reactivity to one another. Estimating reactivity is difficult, and so the Gasteiger charge is used as a proxy. The chemical transformations in this reaction are represented by the following SMILES arbitrary target specification (SMARTS) patterns: [C:1] (=[O:2]) [O:3] [C:4] (=[O:5]). [NH2:6] [Ch:7]>>[C:1] (=[O:2]) [NH:6] ([Ch:7]) [C:4] (=[O:5]) followed by [C:1] (=[0:2]) [0:3] [C:4] (=[O:5])>[N:6]>[C:1] (=[O:2]) [N:6] ([C:4] (=[0:5])) [#0] followed by [NH2:1] [Ch:2]>>[Ch:2] [#]. To minimize the chance of backbiting, proposed polymers in which the shortest path between atoms at each repeat unit edge is fewer than eight atoms were rejected.

Training structure-property models with polyGNN: polyGNN is an approach to training structure-property models. The key elements are multitask learning, neural message passing, and invariance to polymer-specific transformations. By training models to simultaneously learn multiple tasks at once, the risk of generating overfitted predictions for any one specific target property is reduced. As a result, the accuracy for each property is improved. Neural message passing dynamically learns fingerprints during training instead of predefining them. Although an infinite number of features can theoretically be created, the model is incentivized to learn valuable features by minimizing the target property loss through backpropagation. Architectural choices are made to ensure system invariance to translation, addition, and subtraction. These constraints further enhance the quality of learned features. Translation refers to the shift of the periodicity window, resulting in equivalent periodic repeat units such as (—OCC—), (—COC—), and (—CCO—) in polyethylene glycol. Addition (subtraction) involves extending (reducing) a repeat unit by one or more minimal repeat units, as seen in (—COCO—) and (—COCOCO—), which are equivalent repeat units differing only in the addition (or subtraction) of the minimal repeat unit (—CO—).

Using polyGNN, the $T_g$ of polymers was predicted by a four-task model, with the thermal properties melting temperature, decomposition temperature, and thermal conductivity as the supporting tasks. Training data for the band gap model comes from density functional theory (DFT) calculations on both polymer chain and crystal structures. In this work, $E_g$ was predicted at the crystal level. In addition to these two tasks, electron affinity and ionization energy were used as supporting tasks.

$$\in \frac{RT}{100}$$

was predicted using a twelve-task model. This model incorporates the following supporting tasks: room-temperature e at nine frequencies, DFT-computed zero-frequency $\epsilon$, and refractive index from two sources (experiment and DFT).

The solubility of dilute polymer-solvent pairs was predicted using a 61-task machine learning model, one task per solvent. More specifically, the model classifies a polymer-solvent pair as being soluble, partially soluble, or insoluble. The model architecture is identical to the other models, except that the final linear layer outputs a 3-dimensional vector (one dimension per class) instead of a scalar. In addition, a softmax layer is appended to this layer so that the output is in the form of a probability distribution over each class. The model was trained using the same settings proposed in the original polyGNN paper except that the cross-entropy loss was used in this work. The predictions displayed in FIG. 14 were made using a "production" model trained on 26,884 previously-collected data points. Before training the production model, an identical model was trained on two-thirds of the polymer-solvent pairs and tested it on the remaining third. This model achieved an F1-score of 0.724 and an accuracy of 89.7% on all test data. A subset of the test data are made up of polymers not seen during training. This subset contains 800 polymer-solvent pairs and 587 unique polymers in total. Of these 800 pairs with unseen polymers, 30 have ethanol as the solvent and 29 have water. The model achieved an F1-score of 0.738 and an accuracy of 94.9% on all 800 pairs, an F1-score of 1.0 and an accuracy of 100% on the 30 ethanol pairs, and an F1-score of 0.759 and accuracy of 75.4% on the 29 water pairs. The last two scenarios, unseen polymer and water or ethanol, represent the primary use case of the model in the wild.

Counting styrene derivatives: in these examples, the following question is answered: given a palette of f functional groups (e.g., —OH, —F, etc.) to draw from, how many unique styrene derivatives can be made, mathematically? Restricting attention to tri-substituted derivatives $d^{(3)}$, the answer is provided in Equation 2:

$$d^{(3)}(f)=5f^3+f^2 \qquad \text{Equation 2:}$$

Each derivative can either be positionally symmetric about a (see FIG. 15A) or not. An example of a positionally symmetric derivative is (3: $R_1$, 4: $R_2$,5: $R_3$), since the positions 3, 4, 5 are symmetric about a. An example of a positionally asymmetric derivative is (2: $R_1$, 4: $R_2$,5: $R_3$), since the positions 2, 4, 5 are asymmetric about a. As such, Equation 2 becomes Equation 3.

$$d^{(3)}(f)=d^{sym}(f)+d^{asym}(f) \qquad \text{Equation 3:}$$

Figure 15A:
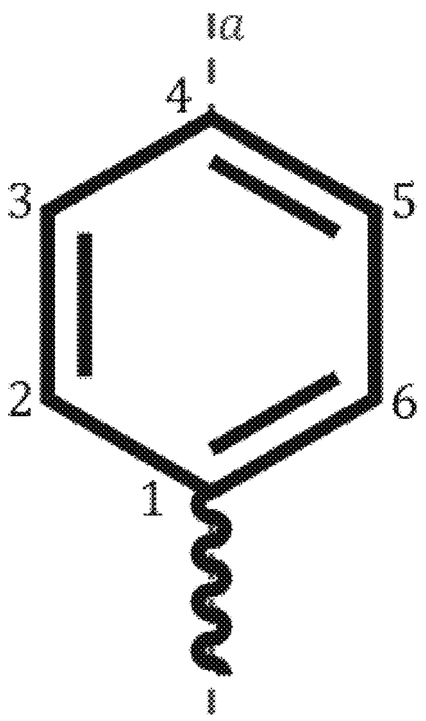
FIG. 15A provides a line drawing of a styrene molecule with the vinyl group at position 1, in accordance with an exemplary embodiment of the present invention.

FIG. 15A shows a styrene molecule with the vinyl group at the 1 position. The numbers represent positions on the benzene ring. Line a represents an axis of symmetry.

First, an expression for $d^{sym}(f)$ is found. There are only two combinations of positions on the styrene molecule that are positionally symmetric about a ($C_{sym}$=2). These positions are (3, 4, 5) and (2, 4, 6). In either case, the 4 position must take on one of the f groups (therefore, the number of combinations $C_4$ for the 4 position is f). This leaves two positions left to be filled with groups from f. For these positions, functional group order does not matter, due to positional symmetry about a. For example, (3: F, 4: F, 5: OH) is equivalent to (3: OH, 4: F, 5: F). Thus, the general equation for number of combinations with replacement $C_R$, which is provided in Equation 4 can be used, where n is the number of objects and r is the number of samples.

$$C_r = \binom{n+r-1}{r} \qquad \text{Equation 4}$$

In this case, n=f and r=2, so $$C_R(f) = \binom{f+1}{2}.$$

Combining these equations yields Equation 5.

$$d^{sym}(f) = C_{sym} \times C_4(f) \times C_R(f) = 2f\binom{f+1}{2} = f^3 + f^2 \qquad \text{Equation 5}$$

Next an expression for $d^{asym}(f)$ is found. For positionally asymmetric derivatives, functional group order does matter. For example, (2: OH, 4: F, 5: OH) is not equivalent to (2: F, 4: OH, 5: OH). There are $$\binom{5}{3} = 10$$

combinations of functional group positions on styrene. Two of these are positionally symmetric about a, leaving 8 positionally asymmetric combinations. Each of these combinations is equivalent to the combination you get when you flip it over the axis a, leading to 4 unique positionally asymmetric combinations. For example, the combination (2: $R_1$, 4: $R_2$, 5: $R_3$) is equivalent to the combination (3: $R_3$, 4: $R_2$, 6: $R_1$). For each unique combination, the number of functional group permutations is $f^3$. Therefore:

$$d^{asym}(f)=4f^3. \qquad \text{Equation 6:}$$

Plugging in Equation 5 and Equation 6 into Equation 3 yields Equation 2.

Figure 15B:
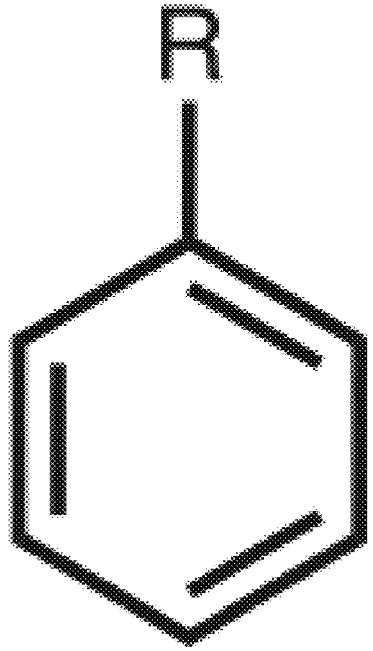
FIG. 15B provides a line drawing of a template for a benzene derivative with the substituent at position 1, in accordance with an exemplary embodiment of the present invention.
Figure 16:
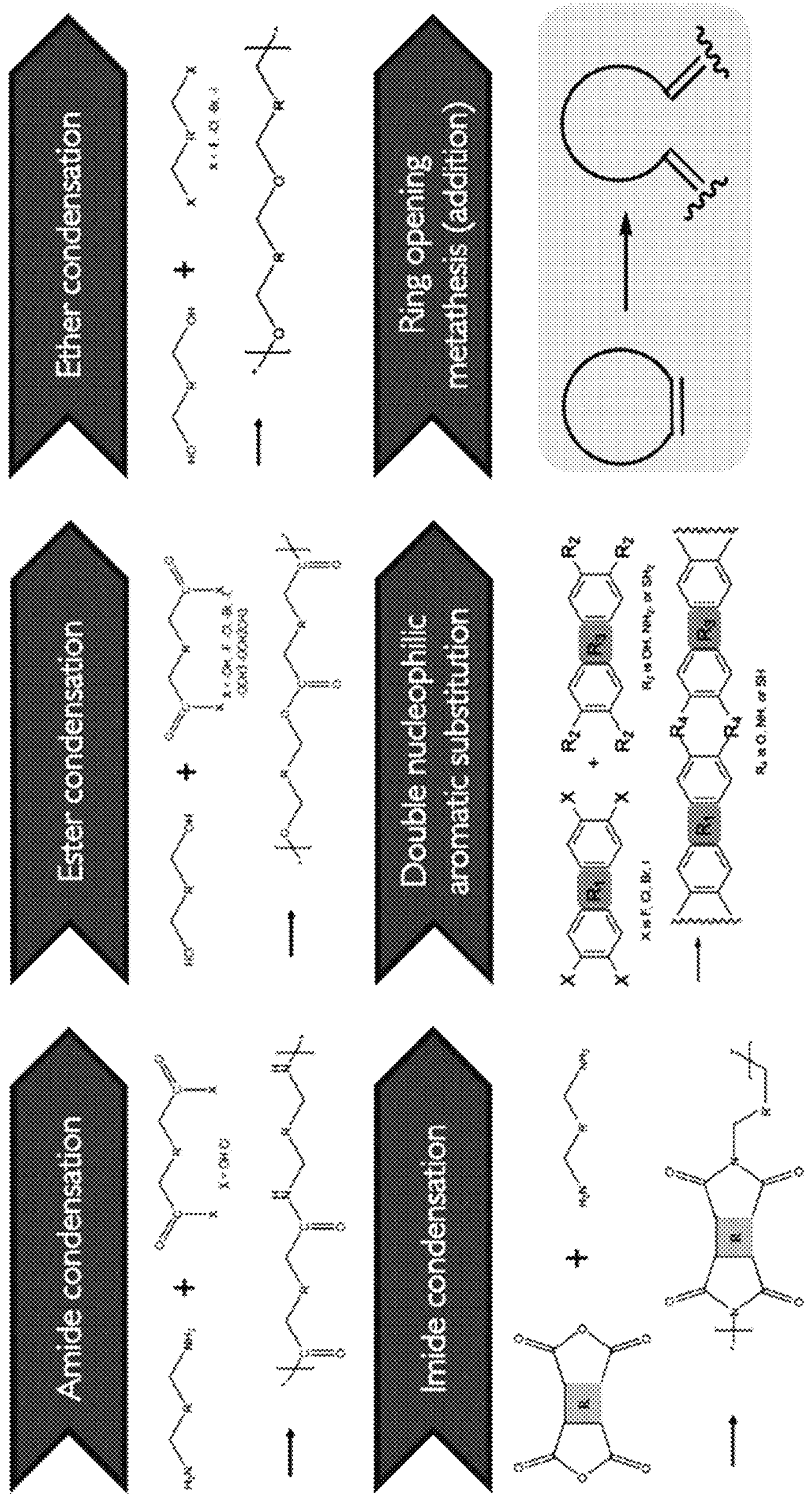
FIG. 16 provides line drawings for various reaction templates, in accordance with an exemplary embodiment of the present invention.
Figure 17:
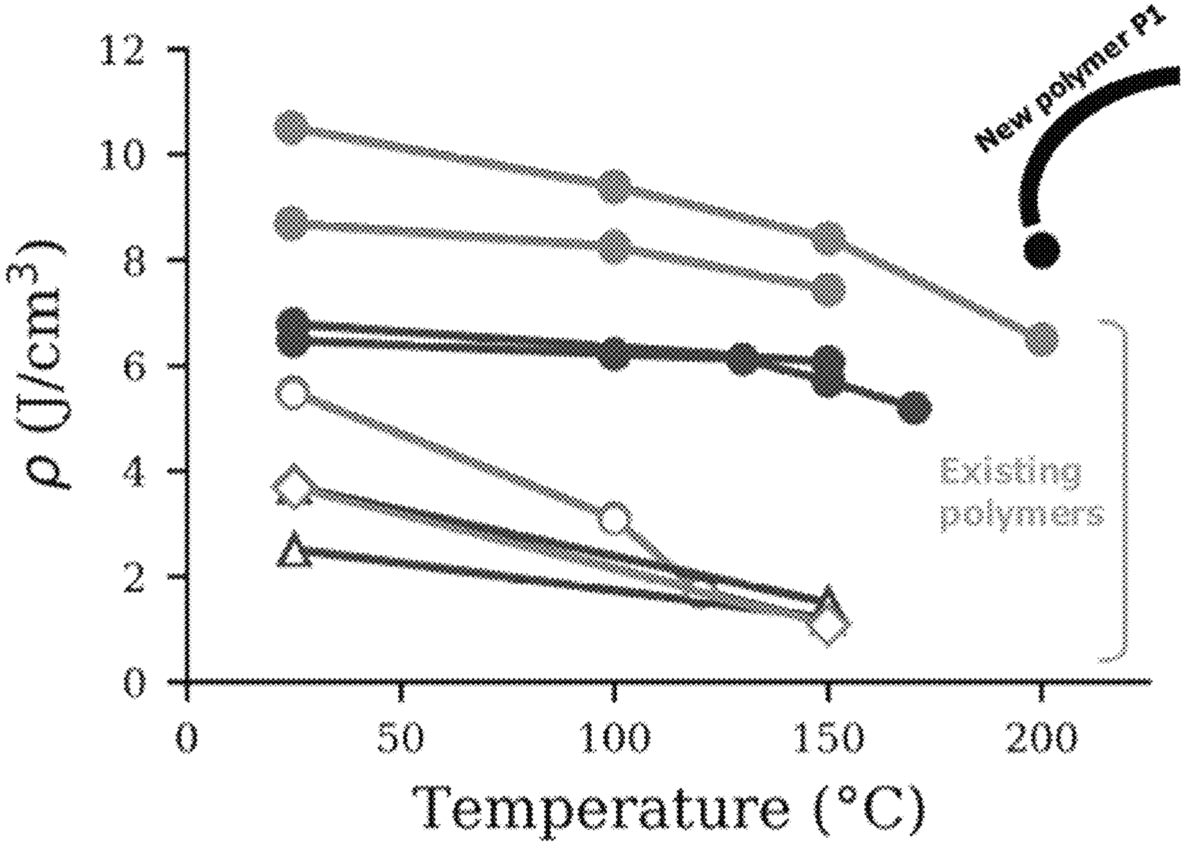
FIG. 17 provides a plot showing charge density versus temperature for commercial polymers and a polymer disclosed herein, in accordance with an exemplary embodiment of the present invention.
Figure 18:
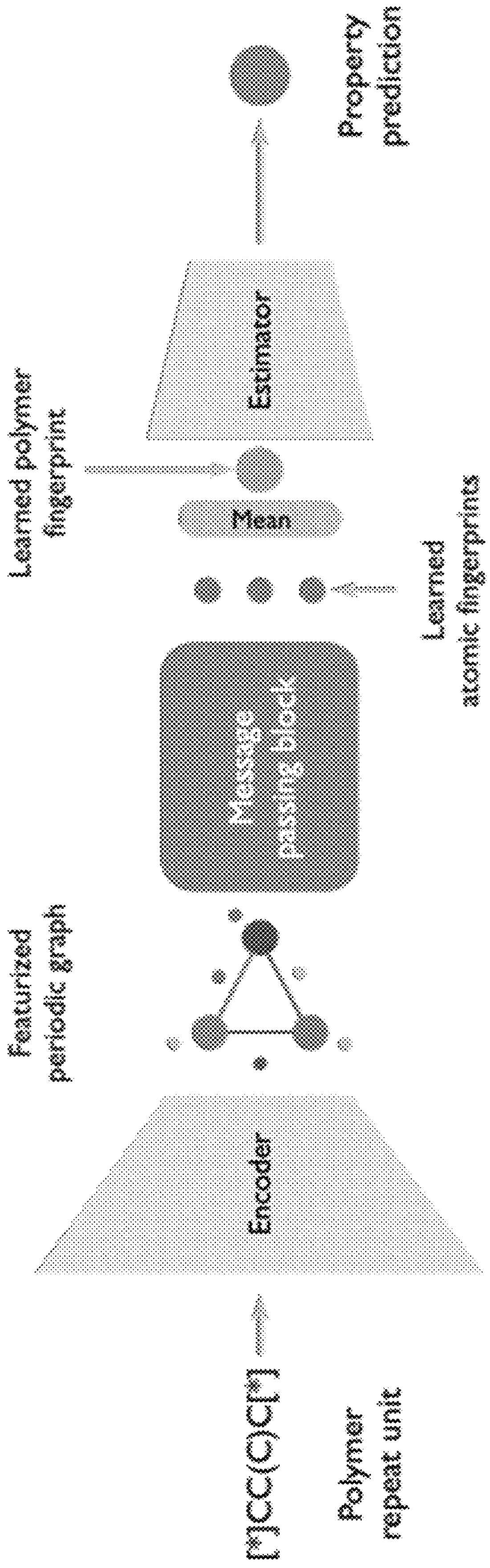
FIG. 18 provides a flowchart for a method of predicting polymer properties, in accordance with an exemplary embodiment of the present invention.
Figure 19:
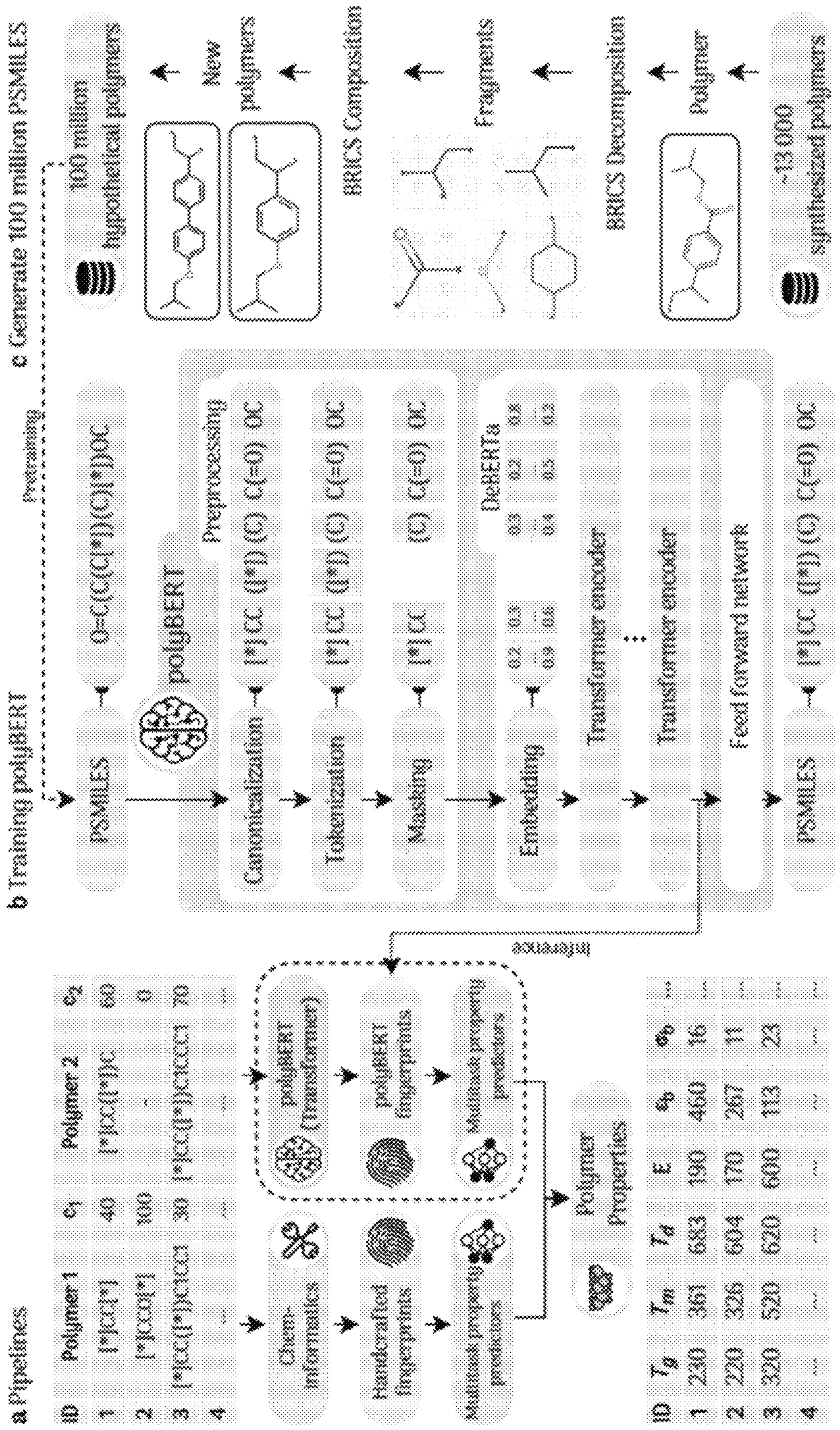
FIG. 19 provides a flowchart for a method of predicting polymer properties, in accordance with an exemplary embodiment of the present invention.
Figure 20:
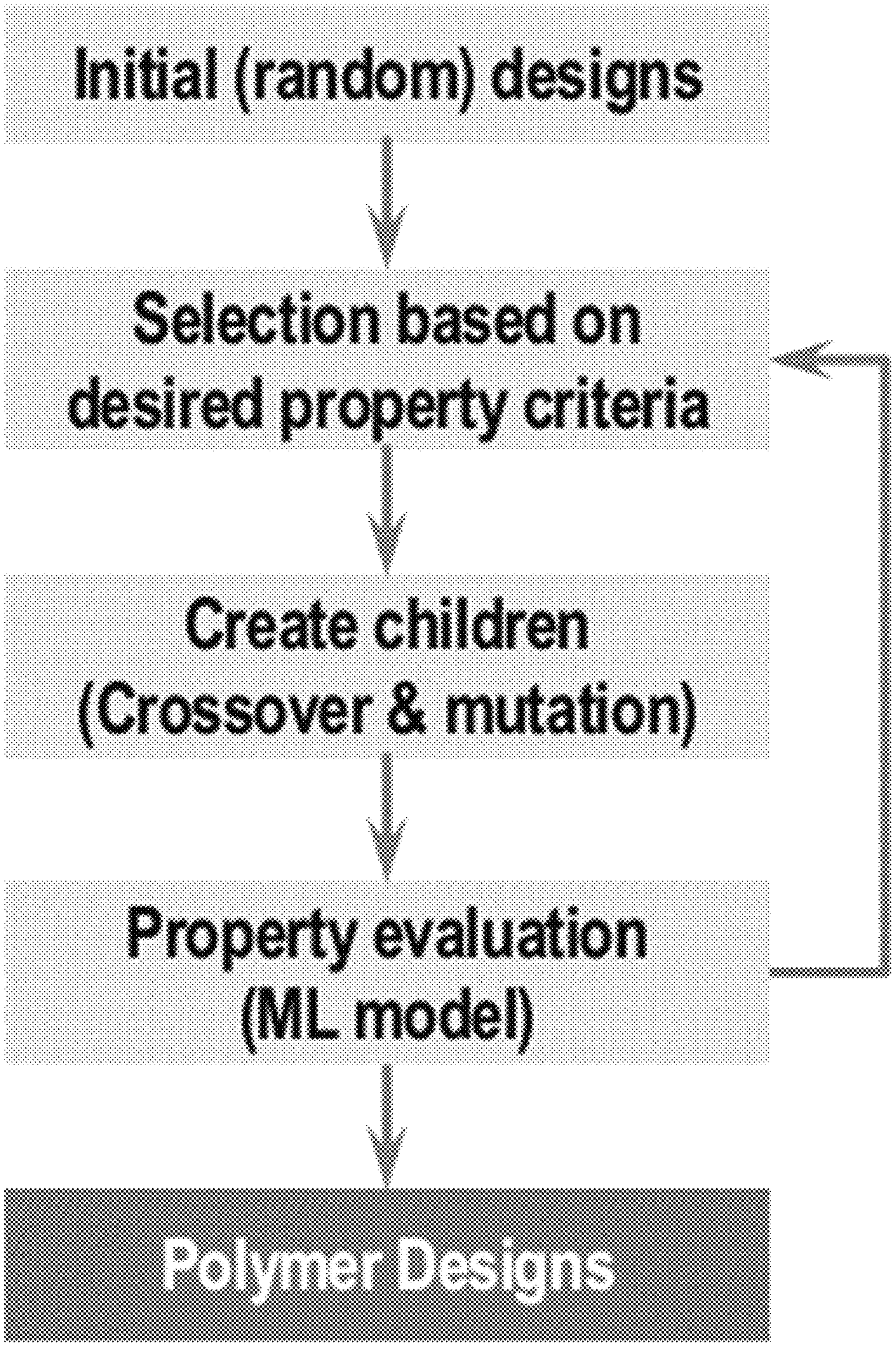
FIG. 20 provides a flowchart for a polymer structure design process, in accordance with an exemplary embodiment of the present invention.
Figure 21:
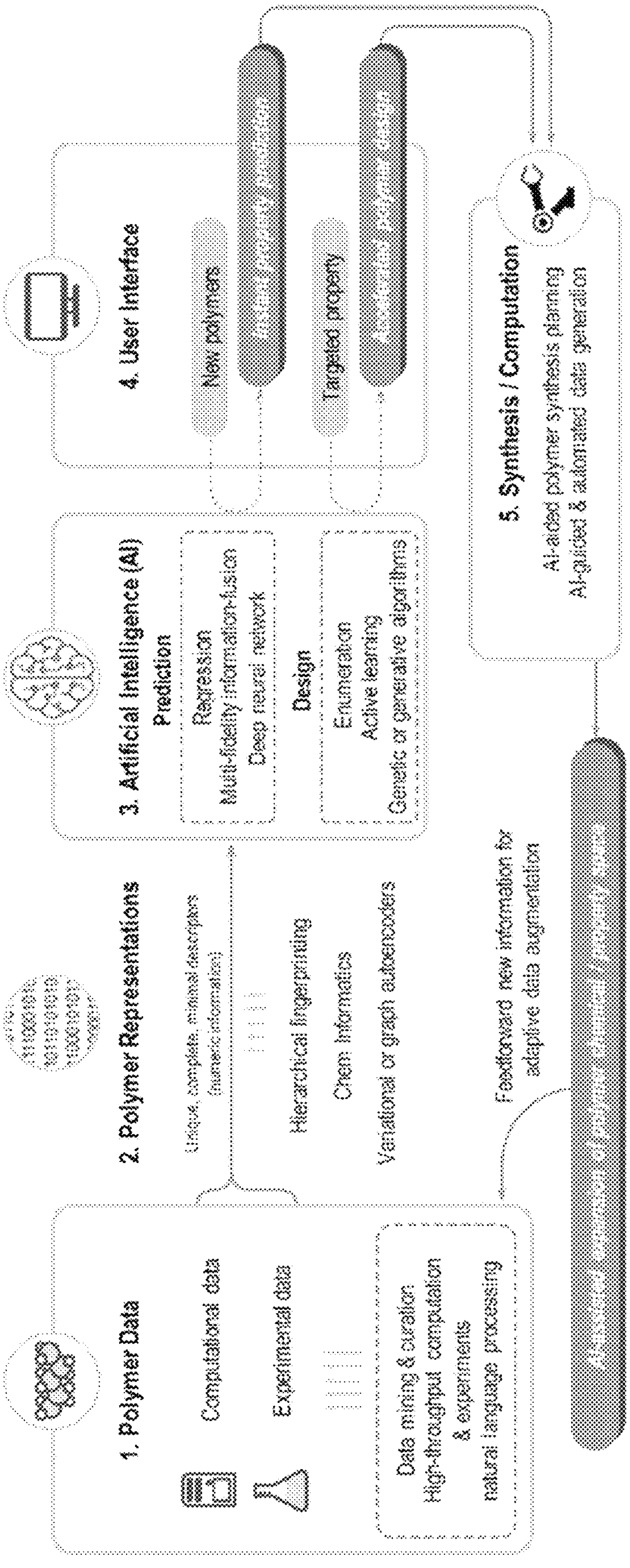
FIG. 21 provides a flowchart for a polymer structure design process in accordance with an exemplary embodiment of the present invention.

This data set of purchasable molecules is used to estimate reasonable values of f. In the data set used herein, there are 56,348 molecules matching the template in FIG. 15B. FIG. 15B provides a template for a benzene derivative. R is any group that does not contain an aromatic ring.

Each match contains a unique functional group. The number of such groups without any double/triple bonds is 5,401. The number of such groups without any rings or double/triple bonds is 2, 274. The number of such groups with four or fewer heavy atoms and no double/triple bonds is 196. These values plugged into these equations yield the following:

$$d^{(3)}(56348)=8.95\times10^{14}$$

$$d^{(3)}(5401)=7.88\times10^{11}$$

$$d^{(3)}(2274)=5.88\times10^{10}$$

$$d^{(3)}(196)=3.77\times10^{7}$$

Considerations of stereochemistry and mono-, di-, tetra-, or penta-substituted styrene derivatives would further increase the population.

Twelve polyVERSE ROMP candidates that were highly ranked by the present polyGNN models were considered for synthesis. Each of these candidates have monomers that are expensive to purchase. Instead, the monomers would need to be synthesized in-house. As an alternative, a separate list was made of candidates with monomers that could be directly purchased for <$20 per gram, and then ranked these by polyGNN prediction. The first four candidates were successfully synthesized.

Comparison of ML predictions and measurements: some polyGNN predictions were validated against experimental measurements carried out in this work. These quantities are listed in Table 2.

TABLE 2

| | Eg, eV | | ϵRT | | Tg, °C | |
|---|---|---|---|---|---|---|
| PONB-2Me5Cl | 4.39 | (4.69) | 3.29 | (4.02) | 232 | (214) |
| PNB-Dimethyl | 4.34 | (4.76) | 3.14 | (3.57) | 232 | (219) |
| PNB-2Me5Cl | 4.32 | (4.61) | 3.06 | (3.80) | 243 | (236) |
| PNB-3Cl4Me | 4.27 | (4.68) | 2.90 | (3.78) | 220 | (228) |

Table 2 shows a comparison of measured and predicted values for three properties. Measured values are shown in plain text and predicted values are shown in parentheses.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A method comprising:

predicting properties of one or more polymer structures from a set of polymer structures;

selecting one or more of the polymer structures from the set of polymer structures based, at least in part, on the predicted properties; and synthesizing a dielectric polymer having one or more of the selected polymer structures and having the following structure:

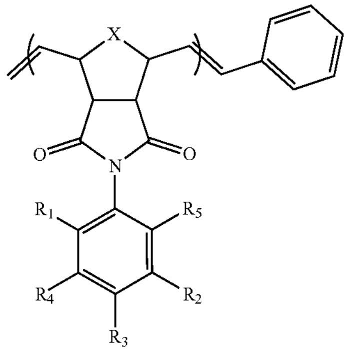

;

wherein X and $R_1$-$R_5$ define a substitution profile selected from a group consisting of:

X is oxygen, $R_1$ is a methyl group, $R_2$ is chlorine, and $R_3$, $R_4$ and $R_5$ are each hydrogen;

X is carbon, $R_1$ is a methyl group, $R_2$ is chlorine, and $R_3$, $R_4$ and $R_5$ are each hydrogen;

X is carbon, $R_2$ is chlorine, $R_3$ is a methyl group, and $R_1$, $R_4$ and $R_5$ are each hydrogen;

X is carbon, $R_1$ and $R_2$ are each a methyl group, and $R_3$, $R_4$ and $R_5$ are each hydrogen; and X is carbon, $R_2$ and $R_5$ are each chlorine, and $R_1$, $R_3$ and $R_4$ are each hydrogen.

2. The method of claim 1, wherein the dielectric polymer has a band gap of at between 4.0 eV and 5.0 eV.

3. The method of claim 1, wherein the dielectric polymer has a $T_g$ of between 200 and 250 °C.

4. The method of claim 1, wherein the dielectric polymer has a dielectric constant in the range of 2.5-3.5.

5. The method of claim 1, wherein the dielectric polymer achieves an energy density of 9 J/cc at 200 °C.

6. The method of claim 1, wherein the dielectric polymer achieves:

an energy density greater than approximately 9 J/cc when the polymer is at a temperature between 0 °C and 100 °C; and an energy density greater than approximately 8 J/cc when the polymer is at a temperature between 100 °C and 200 °C.

7. The method of claim 1 further comprising:

generating the set of polymer structures by:

curating a database of available monomers; and choosing a set of polymerization reactions.

8. The method of claim 7, wherein generating the set of polymer structures further comprises:

simulating a transformation of the available monomers based on the polymerization reactions.

9. The method of claim 1 further comprising:

inputting polymer data and one or more target properties of a polymer to be designed into a machine learning model; and updating the polymer data with the set of polymer structures and the predicted properties.

10. The method of claim 9, wherein a target property from the one or more target properties is selected from a group consisting of melting temperature, decomposition temperature, thermal conductivity, band gap, electron affinity, ionization energy, and solubility.

11. The method of claim 10, wherein the polymer data comprises computational data and experimental data for known polymers.

12. The method of claim 1 further comprising:

providing a set of polymer data, the polymer data including a set of monomer structures; and generating the set of polymer structures by applying one or more reaction templates to the set of monomer structures;

wherein a reaction template from the one or more reaction templates is selected from a group consisting of an amide condensation, an ester condensation, an ether condensation, an imide condensation, a double nucleophilic aromatic substitution, a ring opening metathesis, and a click-chemistry based reaction template.

13. A method of generating and manufacturing a structure for a polymer comprising:

curating a database of commercially-available monomer structures;

simulating a transformation via a selected polymerization reaction of monomer structures selected from a subset of the database of monomer structures into a set of polymer repeat unit structures;

predicting one or more properties of one or more of the polymer repeat unit structures;

selecting a polymer repeat unit structure based on the predicted one or more properties; and synthesizing a dielectric polymer having the selected polymer repeat unit structure;

wherein:

the dielectric polymer has the following structure:

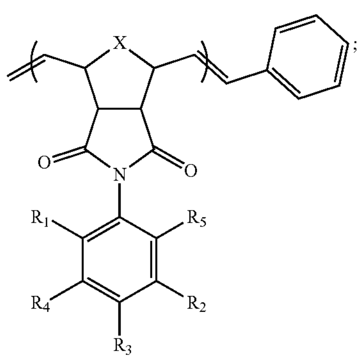

;

and

X and $R_1$-$R_5$ define a substitution profile selected from a group consisting of:

X is oxygen, $R_1$ is a methyl group, $R_2$ is chlorine, and $R_3$, $R_4$ and $R_5$ are each hydrogen;

X is carbon, $R_1$ is a methyl group, $R_2$ is chlorine, and $R_3$, $R_4$ and $R_5$ are each hydrogen;

X is carbon, $R_2$ is chlorine, $R_3$ is a methyl group, and $R_1$, $R_4$ and $R_5$ are each hydrogen;

X is carbon, $R_1$ and $R_2$ are each a methyl group, and $R_3$, $R_4$ and $R_5$ are each hydrogen; and X is carbon, $R_2$ and $R_5$ are each chlorine, and $R_1$, $R_3$ and $R_4$ are each hydrogen.

* * * * *